(12) United States Patent
Kando et al.

(10) Patent No.: US 6,316,477 B1
(45) Date of Patent: *Nov. 13, 2001

(54) ARYLPYRAZOLE INSECTICIDES

(75) Inventors: Yasuyuki Kando; Toshiyuki Kiji; Atsuo Akayama; Makoto Noguchi, all of Tsukuba (JP)

(73) Assignee: Takeda Chemical Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,231
(22) PCT Filed: Jan. 29, 1997
(86) PCT No.: PCT/JP97/00190
  § 371 Date: Jul. 24, 1998
  § 102(e) Date: Jul. 24, 1998
(87) PCT Pub. No.: WO97/28126
  PCT Pub. Date: Aug. 7, 1997

(30) Foreign Application Priority Data

Jan. 30, 1996 (JP) .................................................... 8-014576
Sep. 27, 1996 (JP) .................................................... 8-256261

(51) Int. Cl.⁷ .................... A61K 31/4155; C07D 271/06; C07D 413/04
(52) U.S. Cl. .......................... 514/364; 548/145; 424/409; D16/10
(58) Field of Search ........................... 514/364; 548/145; 424/409

(56) References Cited

U.S. PATENT DOCUMENTS

| | | | |
|---|---|---|---|
| 4,771,066 | 9/1988 | Gehring et al. | 514/404 |
| 5,232,940 | 8/1993 | Hatton et al. | 514/407 |
| 5,236,938 | 8/1993 | Huang et al. | 514/341 |
| 5,306,694 | 4/1994 | Phillips et al. | 504/253 |
| 5,580,843 | 12/1996 | Stetter et al. | 514/341 |

FOREIGN PATENT DOCUMENTS

| | | |
|---|---|---|
| 0 385 809 | 9/1990 | (EP) . |
| 0 659 745 A1 | 6/1995 | (EP) . |
| 8-311036 | 11/1996 | (JP) . |
| 93/06089 | 4/1993 | (WO) . |
| 97/07102 | 2/1997 | (WO) . |

*Primary Examiner*—T. A. Solola
(74) *Attorney, Agent, or Firm*—Wenderoth, Lind & Ponack, L.L.P.

(57) ABSTRACT

A compound of the formula:

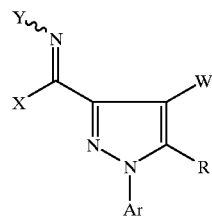

wherein Ar is an optionally substituted aromatic hydrocarbon or aromatic heterocyclic group, R is H, halogen or a group bonded through C, N, O, S or P, W is halogen or a group bonded through C, N, O, S or P, X is H or a group bonded through C, N, O or S, Y is H or a group bonded through C, N, O, S or P, or X and Y together with the adjacent nitrogen atom to Y may form an optionally substituted nitrogen-containing heterocyclic group which may further have N, O, S and/or P, or a salt thereof, a method of production thereof and agrochemicals containing the above compound [I]. The compound [I] and their salts are effective in preventing sanitary or horticultural insect pests and animal and plant parasites and can exert potent insecticidal activities when they are applied to harmed living animals or plants. Moreover, the compounds [I] and their salts possess safe and advantageous properties as agents for preventing sanitary, horticultural or agricultural injurious insects, such as no substantial damage on plants and less toxicity against fishes.

14 Claims, No Drawings

ARYLPYRAZOLE INSECTICIDES

TECHNICAL FIELD

The present invention relates to new 1-arylpyrazole derivatives or their salts, their productions and agrochemical compositions containing the same.

BACKGROUND ART

Although various synthesized compounds having inhibitory actions against harmful pests have hitherto been used as insecticides, almost all of them belong to organic phosphate esters, carbamic esters, organic chlorine-containing compounds or pyrethroid compounds.

On the other hand, it has been reported that 1-arylpyrazole derivatives, wherein the 3-position of a pyrazole ring is a hydrogen atom, an alkyl group, a cycloalkyl group, a halogenoalkyl group, a cyano group, a nitro group, a halogen atom, a carbamoyl group or a thiocarbamoyl group have an insecticidal activity (U.S. Pat. No. 5,232,940 corresponding to JP-A 228065/1987, U.S. Pat. No. 4,771,066 corresponding to JP-A 207259/1987, U.S. Pat. No. 5,236,938 corresponding to JP-A 148240/1993, EP-A 385809, U.S. Pat. No. 5,306,694 and WO93/06089).

These pyrazole derivatives have insecticidal actions, however, they have high toxicities to human beings, domestic animals and fish. Sometimes, the pyrazole derivatives exhibit toxicity to natural enemies of pests, and a high residual property in soil or the like. Therefore, a satisfactory effect is not actually obtained at present.

In order to solve the above problems, the present inventors have intensively studied for a long time so as to find out an insecticide having a structure which is quite different from that of an insecticide which has hitherto been used. As a result, it has been unexpectedly found that a novel pyrazole derivative or a salt thereof has a very strong insecticidal activity. It has also been found that the pyrazole derivative or a salt thereof is safe because it causes little chemical damage to plants and it's toxicity to human being, domestic animals, fish, natural enemies of pests, etc. is low. Furthermore, the present inventors have intensively studied based on these findings and completed the present invention.

DISCLOSURE OF INVENTION

The present invention relates to:
(1) a compound of the formula:

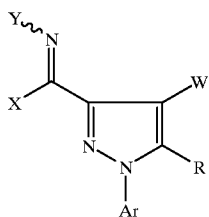

[I]

wherein Ar is an optionally substituted aromatic hydrocarbon group or an optionally substituted aromatic heterocyclic group, R is H, a halogen or a group bonded through C, N, O, S or P, W is a halogen or a group bonded through C, N, O, S or P, X is H or a group bonded through C, N, O or S, Y is H or a group bonded through C, N, O, S or P, or X and Y being combined, a group of the formula

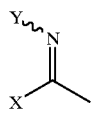

is an optionally substituted nitrogen-containing heterocyclic group which may further have N, O, S and/or P as a ring-constituting atom, or a salt thereof, (2) a process for producing the compound as defined in (1) or a salt thereof which comprises (i) reacting a compound of the formula:

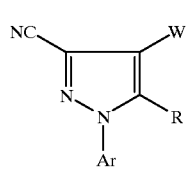

[II]

wherein the symbols are as defined above, or a salt thereof with a compound of the formula:

Q—NH$_2$ wherein Q is a group bonded through C, N, O, S or P, to produce a compound of the formula:

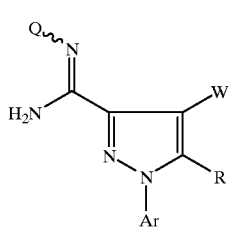

[IV]

wherein the symbols are as defined above, or a salt thereof, or (ii) reacting a compound of the formula:

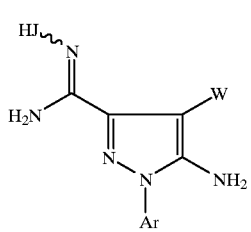

[V]

wherein Ar and W are as defined above, J is O or —NR$^{16}$ (R$^{16}$ is H or a group bonded through C), or a salt thereof with a compound of the formula:

R$^{17}$C(OR$^{18}$)$_3$ wherein R$^{17}$ is H or a C$_{1-6}$ alkyl group, R$^{18}$ is a C$_{1-6}$ alkyl group, to produce a compound of the formula:

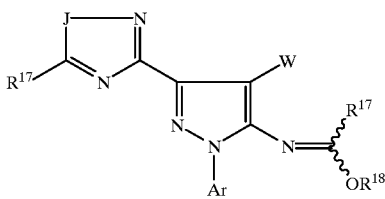

wherein the symbols are as defined above, or a salt thereof, or (iii) oxidizing a compound of the formula:

[XI]

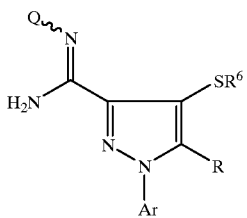

wherein Ar, R and Q are as defined above, $R^6$ is an optionally substituted hydrocarbon group or an optionally substituted heterocyclic group, or a salt thereof, to produce a compound of the formula:

[XII]

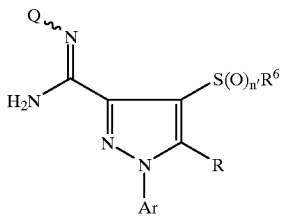

wherein n' is 1 or 2, the other symbols are as defined above, or a salt thereof, or (iv) reacting a compound of the formula:

[XVII]

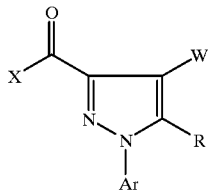

wherein the symbols are as defined above, or a salt thereof with a compound of the formula:

Y—NH$_2$ wherein Y is as defined above, or a salt thereof, to produce a compound of (1) or a salt thereof. (3) an agrochemical composition which comprises an effective amount of the compound as defined in (1) or a salt thereof, and (4) use of the compound of (1) or a salt thereof in the preparation of an insecticidal composition, etc.

The compound of the above formula [I] or a salt thereof of the present invention sometimes have geometrical isomers and/or stereoisomers, and the present invention includes all of these isomers.

In the above formulae, Ar is an optionally substituted aromatic hydrocarbon group or an optionally substituted aromatic heterocyclic group.

Examples of the aromatic hydrocarbon group in the optionally substituted aromatic hydrocarbon group for Ar include a $C_{6-14}$ aromatic hydrocarbon group such as phenyl, naphthyl, biphenylyl, anthryl, phenanthryl and the like.

Examples of the substituent on the aromatic hydrocarbon group include a $C_{1-6}$ alkyl group (e.g. methyl, ethyl, n-propyl, isopropyl, n-butyl, isobutyl, sec-butyl, tert-butyl, n-pentyl, sec-pentyl, isopentyl, n-hexyl), which may optionally be substituted with 1 to 4 substituents selected from the group consisting of, for example, hydroxy, $C_{1-6}$ alkoxy (e.g. methoxy, ethoxy, propoxy, isopropoxy, butoxy, pentyloxy, hexyloxy, etc.), halogen (e.g. fluorine, chlorine, bromine, iodine, etc.) and amino which may optionally be mono- or di-substituted with $C_{1-6}$ alkyl (e.g. methylamino, ethylamino, propylamino, dimethylamino, diethylamino, etc.); an amino group which may optionally be mono- or di-substituted with $C_{1-6}$ alkyl or $C_{1-6}$ alkanoyl (e.g. methylamino, ethylamino, propylamino, dimethylamino, diethylamino, acetylamino, propionylamino, etc.); a hydroxyl group; a carboxyl group; a nitro group; $SF_5$; a $C_{1-6}$ alkoxy group (the same as defined above); a $C_{1-6}$ alkanoyloxy group (e.g. formyloxy, acetyloxy, propionyloxy, n-butyryloxy, iso-butyryloxy, etc.); a cyano group; and a halogen atom (the same as defined above).

The number of substituents is from 1 to 6, preferably from 1 to 4, most preferably from 1 to 3, within the substitutable range. When the substituent is halogen atom, substitution may be performed within the maximum substitutable range.

As the aromatic heterocyclic group in the optionally substituted aromatic heterocyclic group for Ar, for example, 5- to 8-membered aromatic heterocyclic groups having 1 to 4 hetero atoms selected from O, S, N, etc., in addition to carbon atom(s), which may be condensed with a $C_{5-10}$ cyclic hydrocarbon ring (e.g. cyclopentane, cyclohexane, benzene, naphthalene, etc.) or 5- or 6-membered heterocyclic ring having 1 to 4 hetero atoms selected from N, O and S may be used.

Specifically, 5-membered aromatic heterocyclic group having 1 to 4 hetero atoms selected from O, S, N, etc., in addition to carbon atom(s), (e.g. 2- or 3-thienyl, 2- or 3-furyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 1,2,5-thiadiazolyl, 1,2,3-triazolyl, 1,2,4-triazolyl, etc.); 6-membered aromatic heterocyclic group having 1 to 4 hetero atoms selected from O, S, N, etc., in addition to carbon atom(s), (e.g. 2-, 3- or 4-pyridyl or N-oxide thereof, 2-, 4- or 5-pyrimidinyl or N-oxide thereof, 3 or 4-pyridazinyl or N-oxide thereof, pyrazinyl, etc.); and dicyclic or tricyclic condensed aromatic heterocyclic group having 1 to 4 hetero atoms selected from O, S, N, etc., in addition to carbon atom(s), (e.g. benzofuryl, benzothiazolyl, benzoxazolyl, tetrazolo[1,5-b]pyridazinyl, triazolo[4,5-b]pyridazinyl, imidazo[1,2-a]pyridinyl, benzoimidazolyl, quinolyl, isoquinolyl, cinnolinyl, phthalazinyl, quinazolinyl, quinoxalinyl, indolidinyl, quinolidinyl, 1,8-naphthylidinyl, purinyl, pteridinyl, dibenzofuranyl, carbazolyl, acridinyl, phenanthridinyl, chromanyl, benzoxazinyl, phenazinyl, phenothiazinyl, phenoxazinyl, etc.) are used.

As the substituent on the aromatic heterocyclic group, for example, the same substituent as that of the aromatic hydrocarbon group for Ar are used. The number of substituents is from 1 to 6, preferably from 1 to 4, most preferably from 1 to 3, within the substitutable range.

As the halogen atom for W or R, for example, fluorine, chlorine, bromine, iodine, etc are used. Among them, chlorine is preferred.

Examples of the group bonded through C for W, R, X or Y include all organic residues bonded through a carbon atom. For example, an optionally substituted hydrocarbon group, an optionally substituted acyl group, a cyano group, an optionally substituted carbamoyl group, an amidino group or an optionally substituted heterocyclic group having a chemical bond at a carbon atom is used.

As the hydrocarbon group, for example, alkyl group, alkenyl group, alkynyl group, cycloalkyl group, aryl group, aralkyl group, etc. are used. Among them, a $C_{1-24}$ hydrocarbon group is preferred.

As the alkyl group, for example, a $C_{1-15}$ alkyl group (e.g. methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc.) is used. Among them, a $C_{1-6}$ alkyl group such as methyl, ethyl, propyl, isopropyl, butyl, t-butyl, pentyl, hexyl, etc. is particularly preferred. As the alkenyl group, for example, a $C_{2-10}$ alkenyl group (e.g. vinyl, allyl, 2-methylallyl, 2-butenyl, 3-butenyl, 3-octenyl, etc.) is used. Among them, a $C_{2-6}$ alkenyl group such as vinyl, butadienyl, hexatrienyl, etc. is preferred. As the alkynyl group, for example, a $C_{2-10}$ alkynyl group (e.g. ethynyl, 2-propynyl, isopropynyl, butynyl, t-butynyl, 3-hexynyl, etc.) is used. Among them, a $C_{2-6}$ alkynyl group is preferred. As the cycloalkyl, for example, a $C_{3-6}$ cycloalkyl group such as cyclopropyl, cyclopentyl, cyclohexyl, etc. is preferred. As the aryl group, for example, a $C_{6-14}$ aryl group such as phenyl, naphthyl, anthracenyl, etc. is used. As the aralkyl group, for example, a $C_{7-20}$ aralkyl group such as benzyl, phenylethyl, benzhydryl, trityl, etc. is used. Among them, a $C_{7-15}$ aralkyl group is preferred.

These hydrocarbon groups may be substituted with the substituents as described hereinafter. As the substituted hydrocarbon group, for example, an alkoxyalkyl group (e.g. $C_{1-3}$ alkoxy-$C_{1-6}$ alkyl group such as methoxymethyl, ethoxymethyl, ethoxybutyl, propoxymethyl, propoxyhexyl etc.), a hydroxyalkyl group (e.g. hydroxy $C_{1-6}$ alkyl group such as hydroxymethyl, hydroxyethyl, hydroxybutyl, hydroxypropyl, etc.) and a halogenated alkyl group (e.g. mono-, di- or tri-halogenated $C_{1-6}$ alkyl group such as chloromethyl, fluoromethyl, bromomethyl, chloroethyl, dichloromethyl, trichloromethyl, trifluoromethyl, etc.) are preferred.

As the acyl group in the optionally substituted acyl group, for example, an acyl group derived from a $C_{1-24}$ aliphatic carboxylic acid is used. Specifically, for example, a $C_{1-6}$ alkanoyl group such as formyl, acetyl, ethylcarbonyl, propylcarbonyl, tert-butylcarbonyl, etc.; a $C_{1-6}$ alkoxy-carbonyl group such as methoxycarbonyl, ethoxycarbonyl, etc.; a $C_{6-14}$ aryl-carbonyl group such as benzoyl, etc.; a $C_{6-14}$ aryloxy-carbonyl group such as benzoxycarbonyl, etc.; a $C_{7-15}$ aralkyl-carbonyl group such as benzylcarbonyl, etc.; and a $C_{7-15}$ aralkyloxy-carbonyl group such as benzyloxycarbonyl, etc. are used.

As the optionally substituted carbamoyl, for example, a carbamoyl group which may be substituted with an optionally substituted $C_{1-20}$ hydrocarbon group (e.g. $C_{1-15}$ alkyl, $C_{2-10}$ alkenyl, $C_{2-10}$ alkynyl, $C_{7-14}$ aryl or $C_{7-20}$ aralkyl group, etc.) is used. Specifically, a mono- or di-$C_{1-15}$ alkyl-carbamoyl group (e.g. mono- or di-$C_{1-6}$ alkyl-carbamoyl group such as methylcarbamoyl, ethylcarbamoyl, hexylcarbamoyl, dimethylcarbamoyl, methylethylcarbamoyl, etc.) is preferred.

As the heterocyclic group in the optionally substituted heterocyclic group having a chemical bond at a carbon atom, for example, a 3- to 8-membered heterocyclic group having 1 to 4 hetero atoms selected from N, O and S, etc., in addition to carbon atom(s), which may be condensed with a $C_{5-10}$ cyclic hydrocarbon ring (the same as defined above) or 5- or 6-membered heterocyclic ring having 1 to 4 hetero atoms selected from N, O and S are used.

Specifically, 5-membered cyclic group having 1 to 4 hetero atoms selected from O, S and N, in addition to carbon atom(s) (e.g. 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, etc.); 6-membered cyclic group having 1 to 4 hetero atoms selected from O, S and N, in addition to carbon atom(s) (e.g. N-oxide-2-, 3- or 4-pyridyl, 2-, 4- or 5-pyrimidinyl, N-oxide-2-, 4- or 5-pyrimidinyl, 2- or 3-thiomorpholinyl, 2- or 3-morpholinyl, oxotriazinyl, dioxotriazinyl, pyrrolidinyl, piperidinyl, pyranyl, thiopyranyl, 1,4-oxadinyl, 1,4-thiazinyl, 1,3-thiazinyl, 2- or 3-piperazinyl, triazinyl, oxotriazinyl, 3- or 4-pyridazinyl, pyrazinyl, N-oxide-3- or 4-pyridazinyl, etc); and dicyclic or tricyclic condensed aromatic heterocyclic group having 1 to 4 hetero atoms selected from O, S and N in addition to carbon atom (e.g. benzofuryl, benzothiazolyl, benzoxazolyl, tetrazolo[1,5-b]pyridazinyl, triazolo[4,5-b]pyridazinyl, imidazo[1,2-a]pyridinyl, benzoimidazolinyl, quinolyl, isoquinolyl, cinnolinyl, phthalazinyl, quinazolinyl, quinoxalinyl, indolidinyl, quinolidinyl, 1,8-naphthylidinyl, purinyl, pteridinyl, dibenzofuranyl, carbazolyl, acridinyl, phenanthridinyl, chromanyl, benzoxazinyl, phenazinyl, phenothiazinyl, phenoxazinyl, etc.) are used.

These hydrocarbon group, acyl group, carbamoyl group substituted with a $C_{1-20}$ hydrocarbon group and heterocyclic group having a chemical bond at carbon atom may have substituents. As the substituents, for example, a nitro group; a hydroxyl group; an oxo group; a thioxo group; a cyano group; a carbamoyl group; a carboxyl group; a $C_{1-15}$ acyl group [e.g. $C_{1-6}$ alkoxy-carbonyl (methoxycarbonyl, ethoxycarbonyl, n-propoxycarbonyl, iso-propoxycarbonyl, n-butoxycarbonyl, iso-butoxycarbonyl, tert-butoxycarbonyl, etc.), $C_{1-6}$ alkanoyl (e.g. formyl, acetyl, propionyl, n-butyryl, iso-butyryl, etc.), $C_{6-14}$ aryl-carbonyl (e.g. benzoyl, etc.)]; a sulfo group; a halogen atom (the same as defined above); a $C_{1-14}$ hydrocarbon-oxy group [e.g. $C_{1-6}$ alkoxy (the same as defined above), $C_{6-14}$ aryloxy (e.g. phenoxy, naphthyloxy, etc.)] which may optionally be mono- to tri-substituted with halogen (e.g. o-, m- or p-chlorophenoxy, o-, m- or p-bromophenoxy, etc.);—S(O)$_{n''}$R$^a$ wherein n'' is 0, 1 or 2, R$^a$ is a $C_{1-14}$ hydrocarbon group such as $C_{1-6}$ alkyl, $C_{6-14}$ aryl [e.g. $C_{1-6}$ alkylthio (e.g. methylthio, ethylthio, propylthio, isopropylthio, n-butylthio, sec-butylthio, tert-butylthio, etc.), $C_{6-14}$ arylthio (e.g. phenylthio, etc.), $C_{1-6}$ alkylsulfinyl (e.g. methylsulfinyl, ethylsulfinyl, propylsulfinyl, butylsulfinyl, etc.), $C_{1-6}$ alkylsulfonyl (e.g. methylsulfonyl, ethylsulfonyl, propylsulfonyl, butylsulfonyl, etc.)]; an amino group which may optionally be mono- to tri-substituted with $C_{1-6}$ alkyl-carbonyl or $C_{1-6}$ alkyl (e.g. acetylamino, propionylamino, etc.); an imino group which may optionally be substituted with $C_{1-6}$ alkyl, hydroxy or $C_{1-6}$ alkoxy (e.g. methylimino, ethylimino, propylimino, butylimino, methoxyimino, eythoxyimino, n-propoxyimino, etc.); a hydrazono group which may optionally be mono- or di-substituted with $C_{1-4}$ alkyl (e.g. methylhydrazono, ethylhydrazono, dimethylhydrazono, etc.); and 5- or 6-membered heterocyclic group which may have 1 to 4 substituents selected from (a) halogen atom (the same as defined above), (b) $C_{1-4}$ alkyl group (e.g. methyl, ethyl, propyl, isopropyl, etc.) and (c) mono- to tri-halogenated phenoxy group (e.g. o-, m- or p-chlorophenoxy, o-, m- or p-bromophenoxy, etc.) and has 1 to 4 hetero atoms selected from O, S and N, etc., in addition to carbon atom(s) (e.g. 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2- 4- or 5-pyrimidinyl, 3- or 4-pyridazinyl, quinolyl, isoquinolyl, indolyl, etc.) are used. The number of substituents is from 1 to 5, preferably from 1 to 3, within the substitutable range.

Examples of the group bonded through N for W, R, X or Y include all organic residues bonded through a nitrogen atom. For example, (1) a nitro group, (2) a group of the formula: —$NR^1R^2$ wherein $R^1$ and $R^2$ each are H, an optionally substituted hydrocarbon group, an optionally substituted acyl group, an optionally substituted carbamoyl group; an optionally substituted heterocyclic group, a hydroxyl group, an optionally substituted hydrocarbon-oxy group or a group of the formula: —$SOpR^8$ ($R^8$ is H or an optionally substituted hydrocarbon group, and p is 1 or 2), (3) an optionally substituted heterocyclic group having a chemical bond at a nitrogen atom and (4) a group of the formula: —$N=C(R^3)R^4$ wherein $R^3$ and $R^4$ each are H, an optionally substituted hydrocarbon group, an optionally substituted hydrocarbon-oxy group or a group of the formula: —$NR^9R^{10}$ ($R^9$ and $R^{10}$ each are H, a hydroxyl group or an optionally substituted hydrocarbon group) are used.

As the optionally substituted hydrocarbon group for $R^1$, $R^2$, $R^3$, $R^4$, $R^8$, $R^9$ or $R^{10}$, the same one as the above optionally substituted hydrocarbon group defined in the group bonded through C is used.

As the optionally substituted hydrocarbon group of the optionally substituted hydrocarbon-oxy group for $R^1$, $R^2$, $R^3$ or $R^4$, the same one as the above optionally substituted hydrocarbon group defined in the group bonded through C is used.

As the optionally substituted acyl or optionally substituted carbamoyl group for $R^1$ or $R^2$, the same one as the above optionally substituted acyl or optionally substituted carbamoyl group defined in the group bonded through C is used.

As the heterocyclic group in the optionally substituted heterocyclic group for $R^1$ or $R^2$, the same one as the above heterocyclic group defined by the optionally substituted heterocyclic group having a chemical bond at a carbon atom is used.

As the heterocyclic group having a chemical bond at a nitrogen atom defined in the group bonded through N for W, R, X or Y, for example, 3- to 8-membered heterocyclic groups having a chemical bond at a nitrogen atom and 1 to 4 hetero atoms selected from N, O and S in addition to carbon atom(s) and one nitrogen atom which may be condensed with a $C_{5-10}$ cyclic hydrocarbon ring or 5- or 6-membered heterocyclic ring having 1 to 4 hetero atoms selected from N, O and S are used. Specifically, for example, 1H-1-pyrrolyl, 1-imidazolyl, 1-triazolyl, 1-pyrazolyl, 1-indolyl, 1H-indazolyl, 7-purinyl, 1-aziridinyl, 1-pyrrolidinyl, 1-pyrrolinyl, 1-imidazolidinyl, 2-isoxazolidinyl, pyrazolidinyl, piperazinyl, pyrazolinyl, 1-piperidinyl, 4-morpholinyl, 4-thiomorpholinyl, etc. are used.

As the substituent on the heterocyclic group for $R^1$ or $R^2$ and the heterocyclic group having a chemical bond at a nitrogen atom, for example, a $C_{1-20}$ hydrocarbon group [e.g. $C_{1-6}$ alkyl (the same as defined above), $C_{2-6}$ alkenyl (the same as defined above), $C_{2-6}$ alkynyl (the same as defined above), $C_{3-6}$ cycloalkyl (the same as defined above), $C_{5-7}$ cycloalkenyl (e.g. cyclopentenyl, cyclohexenyl, etc.), $C_{7-20}$ aralkyl (the same as defined above), $C_{6-14}$ aryl (the same as defined above)], which may optionally be mono- to tri-substituted with halogen; a $C_{1-4}$ hydrocarbon-oxy group [e.g. $C_{1-6}$ alkoxy (the same as defined above), $C_{6-14}$ aryloxy (the same as defined above)]; a $C_{1-15}$ acyl group [e.g. $C_{1-6}$ alkanoyl (the same as defined above), $C_{6-14}$ aryl-carbonyl (the same as defined above), $C_{1-6}$ alkoxy-carbonyl (the same as defined above)]; a $C_{1-15}$ acyloxy group [e.g. $C_{1-6}$ alkanoyloxy (the same as defined above), $C_{6-14}$ aryl-carbonyloxy (e.g. benzoyloxy, etc.)]; a carboxyl group; a carbamoyl group which may optionally be mono- or di-substituted with $C_{1-4}$ alkyl (e.g. N-methylcarbamoyl, N-ethylcarbamoyl, N-propylcarbamoyl, N-isopropylcarbamoyl, N-butylcarbamoyl, N,N-dimethylcarbamoyl, N,N-diethylcarbamoyl, N,N-dipropylcarbamoyl, N,N-dibutylcarbamoyl, etc.); a cyclic aminocarbonyl group (e.g. 1-aziridinylcarbonyl, 1-azetidinylcarbonyl, 1-pyrrolidinylcarbonyl, 1-piperidinylcarbonyl, N-methylpiperazinyl-carbonyl, morpholinocarbonyl, etc.), a halogen atom (the same as defined above); an oxo group; an amidino group; an imino group which may optionally be substituted with $C_{1-6}$ alkyl group (the same as defined above); an amino group which may optionally be mono- or di-substituted with $C_{1-6}$ alkyl, carbamoyl or N-mono- or N,N-di-$C_{1-4}$ alkyl-carbamoyl (e.g. N-methylcarbamoylamino, N-ethylcarbamoylamino, N-propylcarbamoylamino, N-isopropylcarbamoylamino, N-butylcarbamoylamino, N,N-dimethylcarbamoyl-amino, N,N-diethylcarbamoylamino, etc.); a 3- to 6-membered cyclic amino group having carbon atom(s) and one nitrogen and optionally, 1 to 3 hetero atoms selected from O, S and N (e.g. aziridinyl, azetidinyl, pyrrolidinyl, pyrrolinyl, pyrrolyl, imidazolyl, triazolyl, pyrazolyl, imidazolidinyl, piperidino, morpholino, dihydropyridyl, pyridyl, N-methylpiperazinyl, N-ethylpiperazinyl, etc.); a $C_{1-6}$ alkanoyl-amido group (e.g. formamido, acetamido, trifluoroacetamido, propionylamido, butylylamido, isobutylylamido, etc.); a benzamido group; a $C_{1-3}$ alkylenedioxy group (e.g. methylenedioxy, ethylenedioxy, etc.); —$B(OH)_2$; a hydroxyl group; a nitro group; a cyano group; —$S(O)_{n''}R^b$ wherein n'' is 0, 1 or 2 and $R^b$ is H, hydroxyl or a $C_{1-14}$ hydrocarbon group [e.g. mercapto, sulfo, sulfino, $C_{1-6}$, alkylthio (e.g. methylthio, ethylthio, propylthio, isopropylthio, n-butylthio, sec-butylthio, tert-butylthio, etc.), $C_{6-14}$ arylthio (e.g. phenylthio, etc.), $C_{1-6}$ alkylsulfinyl (e.g. methylsulfinyl, ethylsulfinyl, propylsulfinyl, butylsulfinyl, etc.), $C_{6-14}$ arylsulfinyl (e.g. phenylsulfinyl, etc.), $C_{1-6}$ alkylsulfonyl (e.g. methylsulfonyl, ethylsulfonyl, propylsulfonyl, butylsulfonyl, etc.) and $C_{6-14}$ arylsulfonyl (e.g. phenylsulfonyl, etc.), etc.]; a sulfamoyl group which may optionally be mono- or di-substituted with $C_{1-6}$ alkyl (e.g. N-methylsulfamoyl, N-ethylsulfamoyl, N-propylsulfamoyl, N-isopropylsulfamoyl, N-butylsulfamoyl, N,N-dimethylsulfamoyl, N,N-diethylsulfamoyl, N,N-dipropylsulfamoyl, N,N-dibutylsulfamoyl, etc.), are used. The number of substituents is from 1 to 6, preferably from 1 to 3, within the substitutable range.

Among the above groups bonded through N, for example, (1) a group of the formula: —NR$^{1a}$R$^{2a}$ a wherein R$^{1a}$ is H, an optionally substituted alkyl group, an optionally substituted aralkyl group, an optionally substituted acyl group, an optionally substituted carbamoyl group, an optionally substituted cycloalkyl group, an optionally substituted aryl group, an optionally substituted alkoxy group, an optionally substituted aralkyloxy group, a hydroxy group, an optionally substituted heterocyclic group or —SOpR$^{8a}$ (p is 1 or 2, and R$^{8a}$ is an optionally substituted alkyl group or an optionally substituted aryl group); and R$^{2a}$ is H, an optionally substituted aralkyl group or an optionally substituted alkyl group, (2) a heterocyclic group having a bond at nitrogen atom, such as 1H-1-pyrrolyl, 1-imidazolyl, 1-triazolyl, pyrazolyl, indolyl, 1H-1-indazolyl, 7-purinyl, 1-aziridinyl, 1-pyrrolidinyl, 1-pyrrolinyl, 1-imidazolidinyl, 2-isoxazolidinyl, pyrazolidinyl, piperadinyl, pyrazolinyl, 1-piperazinyl, 4-morpholinyl, 4-thiomorpholinyl, etc. and (3) a group of the formula: —N=C(R$^{3a}$)R$^{4a}$ wherein R$^{3a}$ and R$^{4a}$ each are H, an optionally substituted alkyl group, an optionally substituted aryl group, an optionally substituted alkoxy group, a mono- or di-alkylamino group or a hydroxyamino group, are preferred.

As the alkyl group in the optionally substituted alkyl group for R$^{1a}$, R$^{2a}$, R$^{3a}$, R$^{4a}$ or R$^{8a}$, for example, a C$_{1-6}$ alkyl group such as methyl, ethyl, propyl, isopropyl, butyl, t-butyl, pentyl, hexyl, etc. is used.

As the aralkyl group in the optionally substituted aralkyl group for R$^{1a}$ or R$^{2a}$, for example, a C$_{7-15}$ aralkyl group such as benzyl, phenylethyl, etc. is used.

As the cycloalkyl group in the optionally substituted cycloalkyl group for R$^{1a}$, for example, a C$_{3-6}$ cycloalkyl group such as cyclopropyl, cyclopentyl, cyclohexyl, etc. is used.

As the aryl group in the optionally substituted aryl group for R$^{1a}$, R$^{3a}$, R$^{4a}$ or R$^{8a}$, for example, a C$_{6-14}$ aryl group such as phenyl, naphthyl, anthracenyl, etc. is used.

As the alkoxy group in the optionally substituted alkoxy group for R$^{1a}$, R$^{3a}$ or R$^{4a}$, for example, a C$_{1-6}$ alkoxy group such as methoxy, ethoxy, propoxy, butoxy, etc. is used.

As the aralkyloxy group in the optionally substituted aralkyloxy group for R$^{1a}$, for example, a C$_{7-14}$ aralkyloxy group such as benzyloxy, phenethyloxy, etc. is used.

As the acyl group in the optionally substituted acyl group for R$^{1a}$, for example, a C$_{1-6}$ acyl group such as formyl, acetyl, propionyl, etc. is used.

As the carbamoyl group in the optionally substituted carbamoyl group for R$^{1a}$, the same one as the above optionally substituted carbamoyl group defined in the group bonded through C is used.

As the mono- or di-alkylamino group in the optionally substituted mono- or di-alkylamino group for R$^{3a}$ or R$^{4a}$, for example, a mono- or di-C$_{1-4}$ alkylamino group such as methylamino, ethylamino, dimethylamino, diethylamino, etc. is used.

As the substituent of these alkyl, aralkyl, cycloalkyl, aryl, alkoxy, aralkyloxy, acyl, carbamoyl and mono- or di-alkylamino, for example, the same substituent as that of the hydrocarbon group mentioned for the group bonded through C is used.

As the optionally substituted heterocyclic group for R$^{1a}$, for example, there can be used the same one as the optionally substituted heterocyclic group for R$^1$ or R$^2$.

Examples of the group bonded through O for W, R, X or Y include all organic residues bonded through an oxygen atom. For example, a group of the formula: —OR$^5$ wherein R$^5$ is (1) H, (2) an optionally substituted hydrocarbon group, (3) an optionally substituted heterocyclic group, (4) an optionally substituted acyl group, (5) an optionally substituted carbamoyl group, (6) a group of the formula: —NR$^{11}$R$^{12}$ (R$^{11}$ and R$^{12}$ each are H, an optionally substituted hydrocarbon group or an optionally substituted heterocyclic group) or (7) a group of the formula: —SiR$^{13}{}_3$ (R$^{13}$ is an optionally substituted hydrocarbon group) is used.

As the optionally substituted hydrocarbon group for R$^5$, R$^{11}$, R$^{12}$ or R$^{13}$, for example, the same one as the above optionally substituted hydrocarbon group defined in the group bonded through C is used.

As the optionally substituted heterocyclic group for R$^5$, R$^{11}$ or R$^{12}$, for example, the same one as the above optionally substituted heterocyclic group for R$^1$ or R$^2$ is used.

As the optionally substituted acyl group or the optionally substituted carbamoyl group for R$^5$, for example, the same one as the above optionally substituted acyl group or the above optionally substituted carbamoyl group defined in the group bonded through C is used.

Among the groups bonded through O, for example, a group of the formula: —OR$^{5a}$ wherein R$^{5a}$ is H, an optionally substituted alkyl group, an optionally substituted acyl group, an optionally substituted cycloalkyl group, an optionally substituted aryl group, an optionally substituted heterocyclic group, an optionally substituted arylcarbonyl group, an optionally substituted alkoxycarbonyl group, an optionally substituted aryloxycarbonyl group, an optionally substituted carbamoyl group, a group of the formula: —NR$^{11a}$R$^{12a}$ (R$^{11a}$ and R$^{12a}$ are the same as defined for R$^{1a}$ and R$^{2a}$) or a group of the formula: —SiR$^{13a}{}_3$ (R$^{13a}$ is an alkyl group) is preferred.

The optionally substituted alkyl, acyl, carbamoyl, cycloalkyl, aryl or heterocyclic group for R$^{5a}$ is the same as those for R$^{1a}$.

As the arylcarbonyl group in the optionally substituted arylcarbonyl group for R$^{5a}$, for example, a C$_{6-14}$ arylcarbonyl group such as benzoyl, etc. is used.

As the alkoxycarbonyl group in the optionally substituted alkoxycarbonyl group for R$^{5a}$, for example, a C$_{1-6}$ alkoxycarbonyl group such as methoxycarbonyl, ethoxycarbonyl, etc. is used.

As the aryloxycarbonyl group in the optionally substituted aryloxycarbonyl group for R$^{5a}$, for example, a C$_{6-14}$ aryloxy-carbonyl group such as phenoxycarbonyl, etc. is used.

As the substituent of these arylcarbonyl, alkoxycarbonyl and aryloxycarbonyl, for example, the same substituent of the hydrocarbon group mentioned for the group bonded through C are used.

Examples of the group bonded through S for W, R, X or Y include all organic residues bonded through a sulfur atom. For example, a group of the formula: —S(O)nR$^6$ wherein R$^6$ is an optionally substituted hydrocarbon group or an optionally substituted heterocyclic group, and n is an integer of 0 to 2 is used.

As the optionally substituted hydrocarbon group for R$^6$, for example, the same one as the above optionally substituted hydrocarbon group defined in the group bonded through C is used.

As the optionally substituted heterocyclic group for R$^6$, for example, the same one as the above optionally substituted heterocyclic group for R$^1$ or R$^2$ is used.

Among the groups bonded through S, for example, an optionally substituted alkylthio group, an optionally substituted cycloalkylthio group, an optionally substituted arylthio group, an optionally substituted aralkylthio group, an optionally substituted heterocyclic thio group, an optionally substituted alkylsulfinyl group, an optionally substituted alkylsulfonyl group and an optionally substituted arylsulfonyl group are preferred.

As the optionally substituted alkyl, cycloalkyl, aryl, aralkyl or heterocyclic group in the optionally substituted alkylthio group, optionally substituted cycloalkylthio group, optionally substituted arylthio group, optionally substituted heterocyclic thio group, optionally substituted alkylsulfinyl group, optionally substituted alkylsulfonyl group or optionally substituted arylsulfonyl group, for example, the same one as that for $R^{1a}$ is used.

As the aralkyl group in the optionally substituted aralkylthio group, for example, a $C_{7-15}$ aralkyl group such as benzyl, phenylethyl, etc. is used. As the substituent of the aralkyl group, for example, the same substituent as that of the hydrocarbon group mentioned for group bonded through C is used.

Examples of the group bonded through P for W, R or Y include all groups bonded through a phosphorous atom. For example, a group of the formula: —PO(OR$^7$)$_2$ wherein $R^7$ is H or an alkyl group is used.

As the alkyl group for $R^7$, for example, a $C_{1-15}$ alkyl group such as methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc. is used.

Among the groups bonded through P, for example, a $C_{2-12}$ dialkylphosphono group such as diethylphosphono, dimethylphosphono, etc. is preferred.

As the nitrogen-containing heterocyclic group of the optionally substituted nitrogen-containing heterocyclic group of the formula:

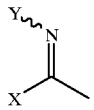

formed by combining X with Y, which may have N, O, S and/or P as a ring-constituting atom, for example, 5- to 8-membered nitrogen-containing heterocyclic groups which may have 1 to 3 hetero atoms selected from N, O, S and P, etc., in addition to one carbon atom are used.

Specifically, a group of the formula:

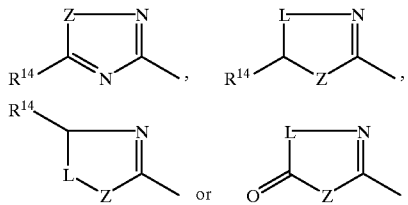

wherein $R^{14}$ is H or an optionally substituted hydrocarbon group; L is O or a $C_{1-3}$ alkylene group (e.g. methylene, ethylene, etc.); and Z is O or a group of the formula: —NR$^{15}$ (R$^{15}$ is H or an optionally substituted hydrocarbon group) is used.

As the optionally substituted hydrocarbon group for $R^{14}$ or $R^{15}$, for example, the same one as the above optionally substituted hydrocarbon group defined in the group bonded through C is used. Among them, a $C_{1-6}$ alkyl group such as methyl, ethyl, propyl, etc. is preferred.

More specifically, as the nitrogen-containing heterocyclic group formed by combining X with Y, for example, a group of the formula:

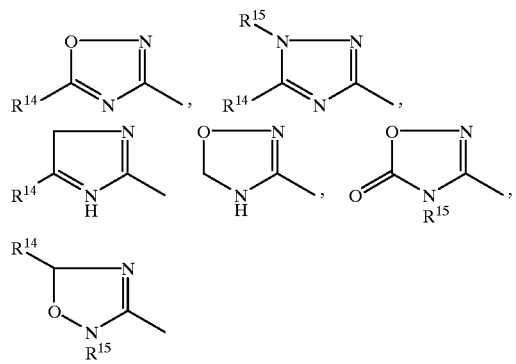

wherein the symbols are as defined above is used.

In the above formulae, Ar is preferably an optionally substituted aromatic hydrocarbon group. The aromatic hydrocarbon group is preferably a $C_{6-14}$ aromatic hydrocarbon group (e.g. phenyl, naphthyl, anthryl, etc.), more preferably a $C_{6-12}$ aromatic hydrocarbon group (e.g. phenyl, etc.). As the substituent, for example, a halogen atom, a $C_{1-6}$ alkyl group and a mono-, di- or tri-halogenated $C_{1-6}$ alkyl group are preferred. The number of the substituents is preferably 1 to 4. Particularly, 2,6-dihalogenophenyl group substituted with a $C_{1-6}$ alkyl group and/or a mono-, di- or tri-halogenated $C_{1-6}$ alkyl group is preferred. As Ar, 2,6-dichloro-4-trifluoromethylphenyl is most preferred.

R is preferably a group bonded through N. Among them, a group of the formula: —NR$^{1b}$R$^{2b}$ wherein R$^{1b}$ and R$^{2b}$ each are H, an optionally substituted $C^{1-20}$ hydrocarbon group (e.g. $C_{1-15}$ alkyl, $C_{6-14}$ aryl, $C_{7-20}$ aralkyl), an optionally substituted mono- or di-$C_{1-4}$ alkyl-carbamoyl group, or an optionally substituted $C_{1-7}$ acyl group (e.g. $C_{1-6}$ alkanoyl, benzoyl), or a group of the formula: —N=C(R$^{3b}$)R$^{4b}$ wherein R$^{3b}$ and R$^{4b}$ each are H; a $C_{1-15}$ alkyl group; a $C_{6-14}$ aryl group which may optionally be substituted with $C_{1-4}$ alkoxy and/or hydroxyl; a $C_{1-15}$ alkoxy group; a mono- or di-$C_{1-15}$ alkylamino group or a hydroxylamino group is preferred. As the substituent of the $C_{1-20}$ hydrocarbon group, mono- or di-$C_{1-4}$ alkyl-carbamoyl group or $C_{1-7}$ acyl group, the same substituent as that of the hydrocarbon group mentioned for the group bonded through C is used. The number of substituents is from 1 to 3, preferably form 1 or 2. It is more preferred that R$^{1b}$ and R$^{2b}$ each are H, a $C_{1-6}$ alkyl group, a $C_{7-15}$ aralkyl group, a mono- or di-$C_{1-4}$ alkyl-carbamoyl group or a $C_{1-7}$ acyl group and R$^{3b}$ is H or a $C_{1-6}$ alkyl group and, further, and R$^{4b}$ is a $C_{2-4}$ alkoxy group, a $C_{6-14}$ aryl group, a mono- or di-$C_{1-4}$ alkylamino group or a hydroxyamino group. As R, an amino group, a mono- or di-$C_{1-4}$ alkylamino group, and a group of —N=CHOCH$_3$ or —N=CHOCH$_2$CH$_3$ are particularly preferred.

W is preferably not a group of the formula:

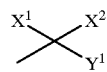

wherein $X^1$ is an optionally substituted haloalkyl group; $X^2$ is H, or a group bonded through C, N, O, S or P; $Y^1$ is a group bonded through N, O, S or P, an optionally substituted aryl group, an optionally substituted heterocyclic group bonded with a carbon atom, or an alkyl group substituted with a cyano, nitro, alkoxycarbonyl or optionally substituted carbamoyl group; and $X^2$ and $Y^1$ may be combined to form a thioxo group, a hydroxyimino group or an oxirane ring, and R and $Y^1$ may be combined to form an optionally substituted $C_{2-4}$ alkylene or $C_{2-4}$ alkenylene group whose constituent carbon atom is substituted with at least one hetero atom selected from O, N, S and P.

W is more preferably a halogen atom, or a group bonded through N, O, S or P. A group of the formula: —S(O)nR$^6$ wherein $R^6$ and n are as defined above is particularly preferred. As the hydrocarbon group represented by $R^6$, for example, a $C_{1-24}$ hydrocarbon group is preferred. Among them, a $C_{1-15}$ alkyl group is more preferred. More specifically, $R^6$ is preferably a $C_{1-6}$ alkyl group which may optionally be substituted with 1 to 4 halogen atoms. As $R^6$, trifluoromethyl is most preffered.

X is preferably a group bonded through N. Among them, a group of the formula —NR$^{1c}$R$^{2c}$ wherein $R^{1c}$ and $R^{2c}$ each are H, a hydroxyl group, an optionally substituted $C_{1-20}$ hydrocarbon group (e.g. $C_{1-15}$ alkyl, $C_{6-14}$ aryl, $C_{7-20}$ aralkyl) or an optionally substituted $C_{1-15}$ acyl group is more preferred. As the substituent of the $C_{1-20}$ hydrocarbon group or $C_{1-15}$ acyl group, the same substituent as that of the hydrocarbon group mentioned for the group bonded through C is used. The number of substituents is from 1 to 3, preferably from 1 or 2. $R^{1c}$ and $R^{2c}$ each are preferably H, hydroxyl group, a $C_{1-6}$ alkyl group or a $C_{1-6}$ acyl group. Particularly, X is preferably amino, mono- or di-methylamino, acetylamino, N-hydroxy-N-methylamino, etc.

Y is preferably H or a group bonded through C, N or O. Among them, H, a hydroxyl group, an optionally substituted $C_{1-15}$ acyloxy group, an optionally substituted mono- or di-$C_{1-4}$ alkyl-carbamoyloxy group, an optionally substituted $C_{1-15}$ alkoxy group, an optionally substituted $C_{1-15}$ acyl group or a group of the formula: —NR$^{1d}$R$^{2d}$ wherein $R^{1d}$ and $R^{2d}$ each are H, or an optionally substituted $C_{1-20}$ hydrocarbon (e.g. $C_{1-15}$ alkyl, $C_{6-14}$ aryl, $C_{7-20}$ aralkyl) or $C_{1-15}$ acyl group is preferred. As the substituent of the $C_{1-15}$ acyloxy, mono- or di-$C_{1-14}$ alkyl-carbamoyloxy, $C_{1-15}$ alkoxy, $C_{1-15}$ acyl or $C_{1-20}$ hydrocarbon group, the same substituent as that of the hydrocarbon group mentioned for the group bonded through C is used. The number of substituents is from 1 to 3, preferably from 1 or 2. More specifically, Y is preferably H; a group bonded through O such as a hydroxyl, $C_{1-15}$ acyloxy (preferably $C_{1-6}$ alkanoyloxy which may be mono- to tri-substituted with halogen; mono- or di-$C_{1-4}$ alkyl-carbamoyloxy, $C_{1-6}$ alkoxy-carbonyloxy; $C_{6-14}$ aryl-carbonyloxy which may be substituted with $C_{1-6}$ alkyl) $C_{1-15}$ alkoxy (preferably, $C_{1-6}$ alkoxy) which may be mono- or di-substituted with $C_{1-4}$ alkoxy; a group bonded through N such as a group of the formula: -NR$^{1d'}$R$^{2d'}$ wherein $R^{1d'}$ and $R^{2d'}$ each are H, $C_{1-6}$ alkyl, $C_{1-6}$ alkanoyl or $C_{1-6}$ alkoxy-carbonyl; a group bonded through C such as $C_{1-15}$ alkyl (preferably, $C_{1-6}$ alkyl), etc.

When W is a group bonded through S, a halogen atom or a nitro group and X is a hydroxyl group or a thiol group, Y is a group other than a hydrogen atom, i.e. preferably group bonded through C, N, O, S or P. In this case, as Y, a group bonded through C exclusive of an substituted alkyl group, a group bonded through N, a group bonded through O, a group bonded through S, or a group bonded through P is preferred.

Specifically, when W is a group bonded through S, a halogen atom or a nitro group, X is a group other than a hydroxyl group and a thiol group.

Specifically, as the optionally substituted nitrogen-containing heterocyclic group formed by combining X with Y, for example, a group of the formula:

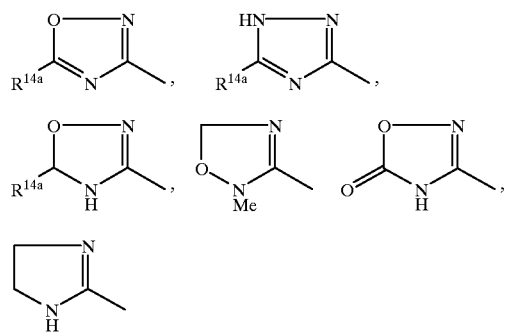

wherein $R^{14a}$ is H or a $C_{1-6}$ alkyl group is preferred.
As the group of the formula:

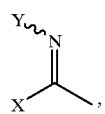

1,2,4-oxadiazol-3-yl is most preferred.

The compound [I] or a salt thereof of the present invention can be produced by the following method.

When the compound [I] can be obtained as a free form or a salt by the following producing method, it can be converted into the above-described salt or free form by conventional methods, respectively. When a compound included in the compound [I] is used as a starting material for producing the other kind of the compound [I], it may be used as it is in the free form or used as the salt. When the other starting material can be the above-described salt, it can also be used as it is in the free form or used as the salt. Accordingly, the starting compounds and products used for the following producing method include their salts (e.g. salts with the acids described with respect to the above compound [I]).

Reaction Scheme (A)
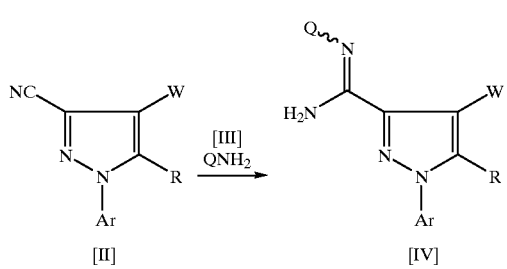
Reaction Scheme (B)
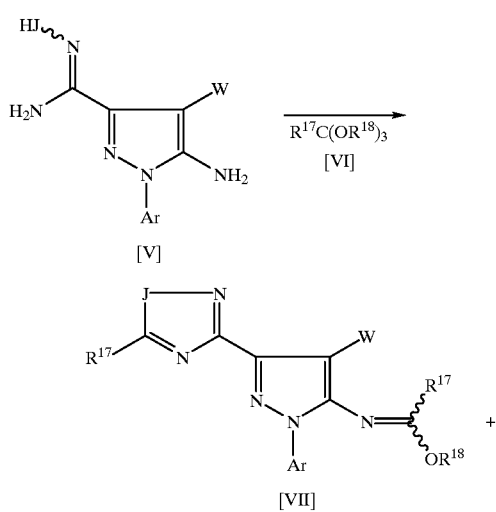
Reaction Scheme (C)
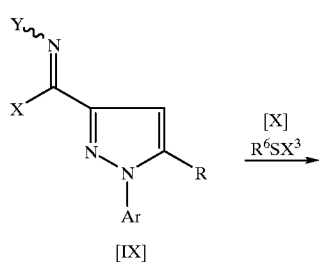
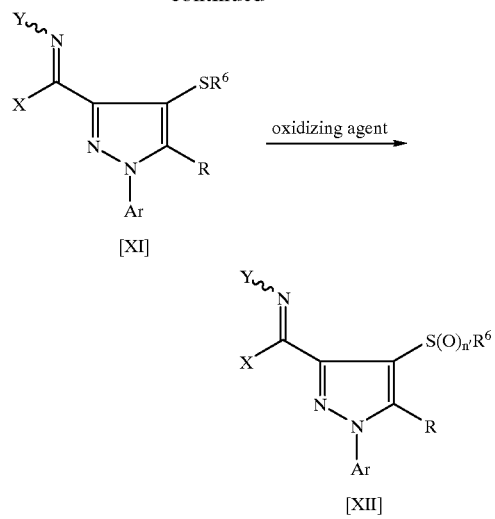
Reaction Scheme (D)
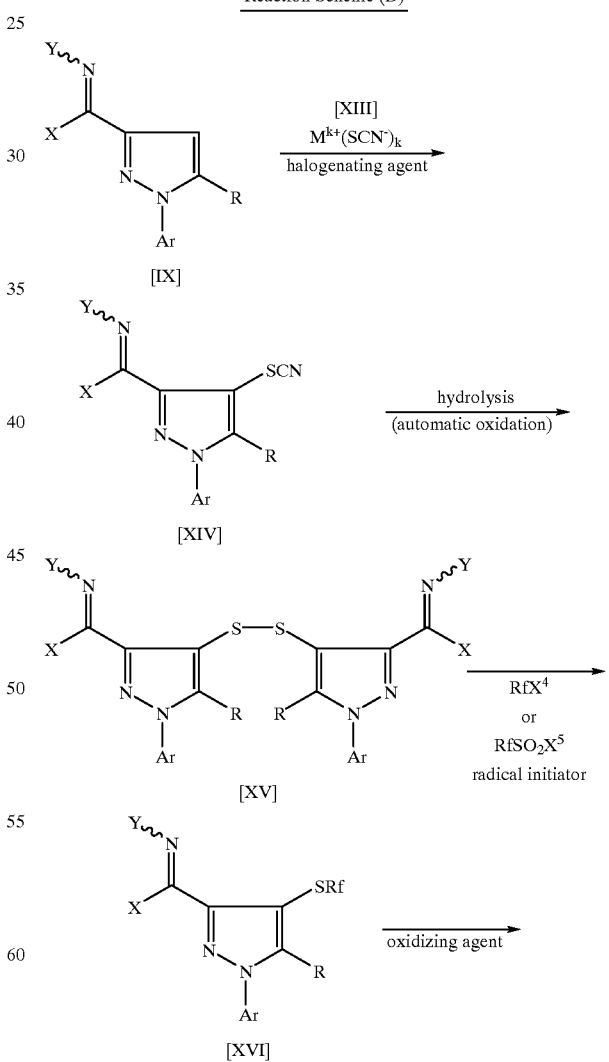

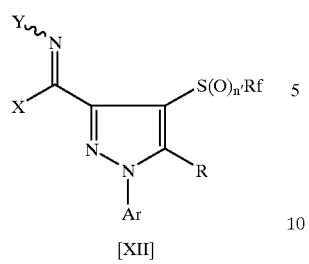
[XII]
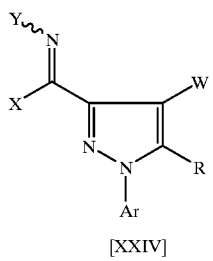
[XXIV]
Reaction Scheme (E)
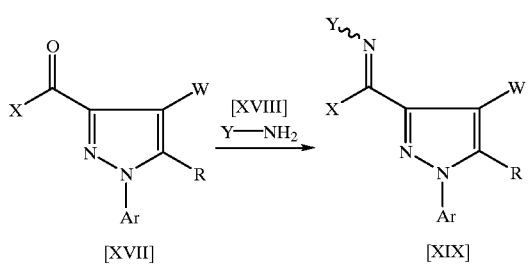
[XVII]    [XIX]
Reaction Scheme (G)
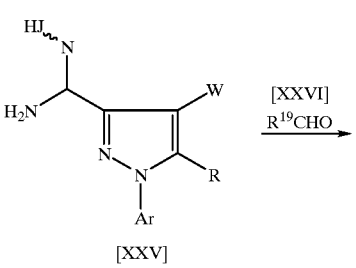
[XXV]
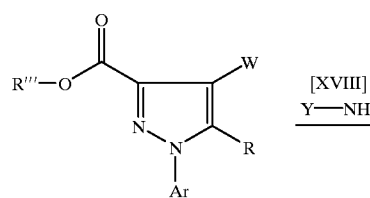
[XXVII]
Reaction Scheme (F)
[XX]
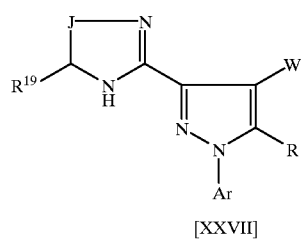
[VIIa]
[XXI]
[XXII]
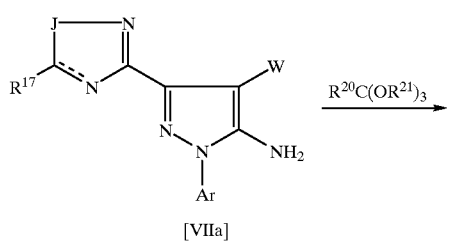
[XXVIII]
( ----- ; single or double bond)

Reaction Scheme (I)
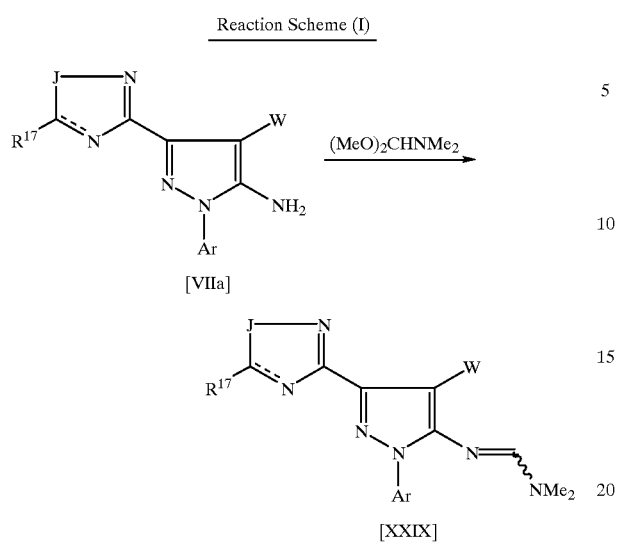
( - - - - ; single or double bond)
Reaction Scheme (J)
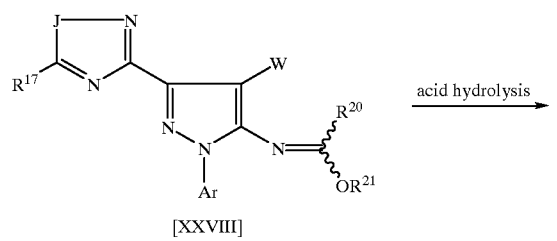
Reaction Scheme (K)
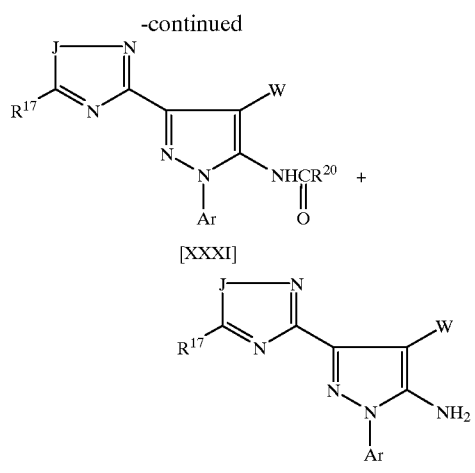
Reaction Schema (L)
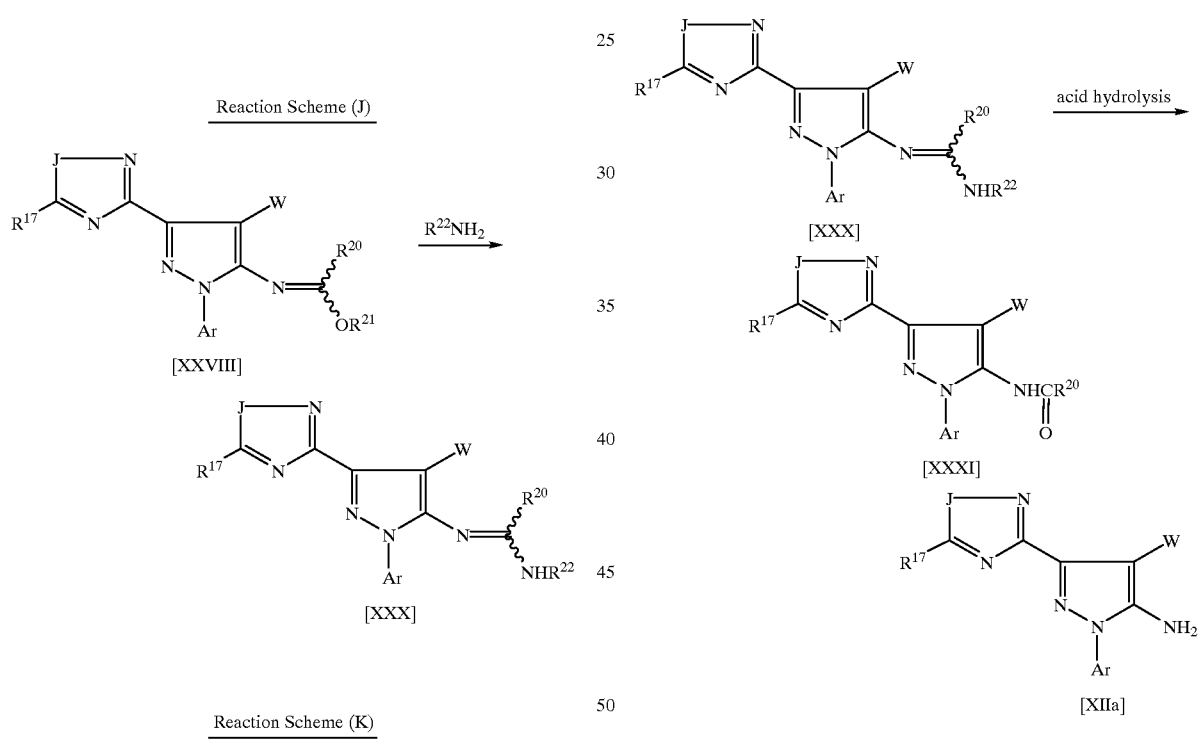
Reaction Schema (M)
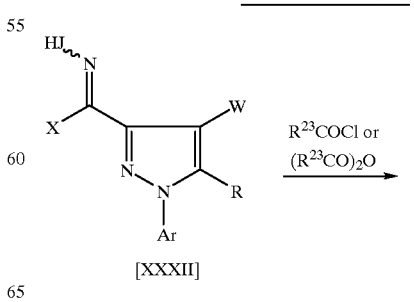

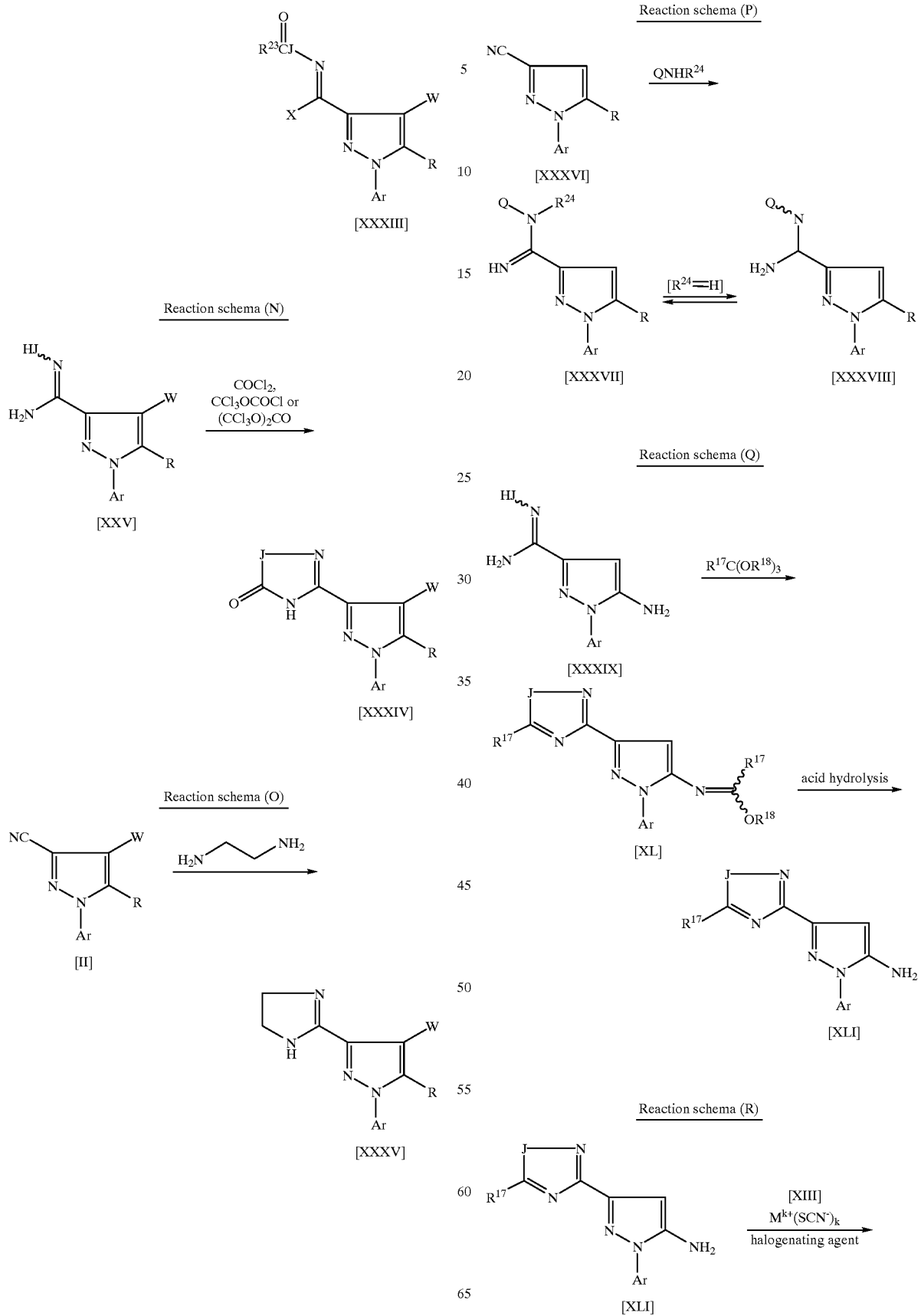

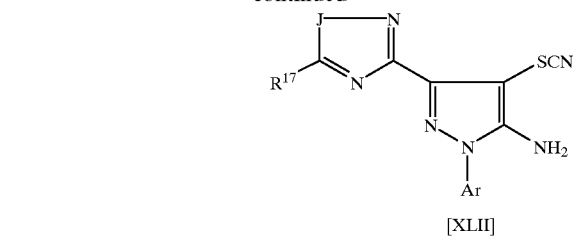
[XLII]
Reaction schema (U)
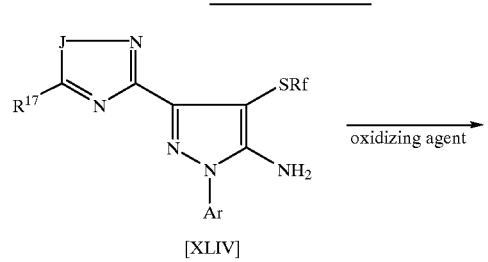
Reaction schema (S)
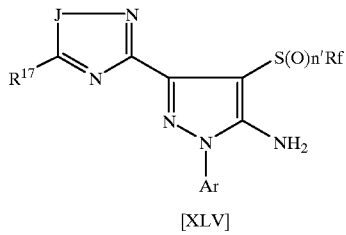
[XLV]
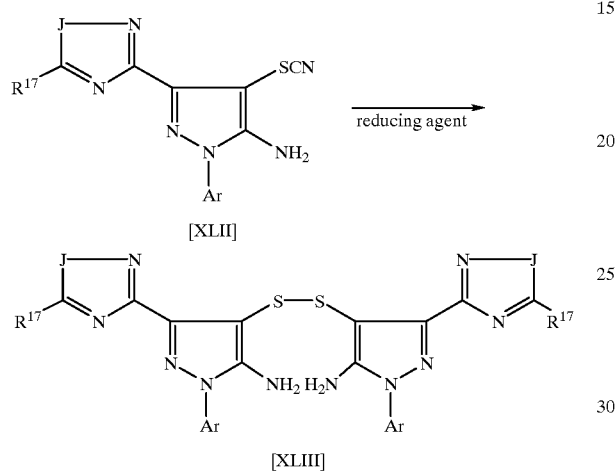
Reaction schema (T)
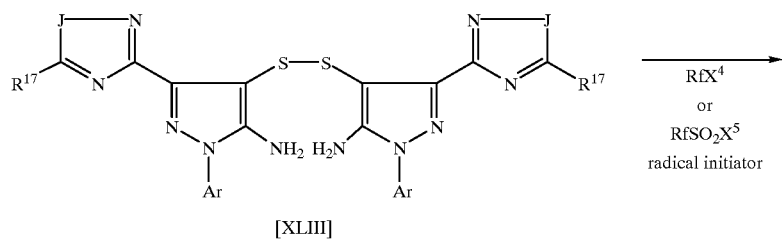
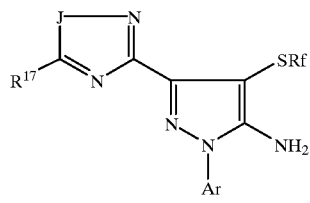
[XLIV]

Reaction schema (V)

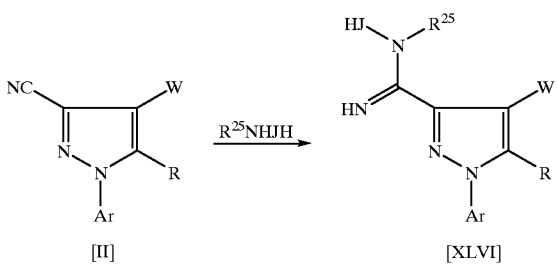

Reaction schema (W)

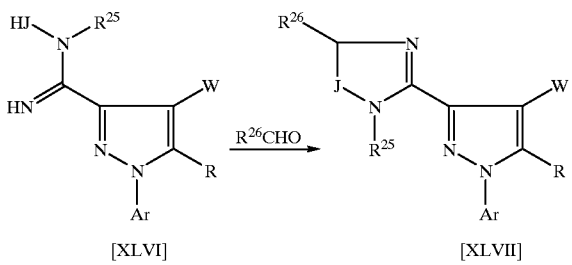

In Reaction schemata (A) to (W), Ar, R, X, Y, W, $R^6$, $R^{17}$, $R^{18}$, n', Q and J are as defined above.

In Reaction schemata (C), (D), and (T), $X^3$, $X^4$ and $X^5$ each are a halogen atom.

In Reaction schemata (G), (H), (J), (K), (L), (P) and (W), $R^{19}$, $R^{20}$, $R^{24}$ and $R^{26}$ each are H or a $C_{1-6}$ alkyl group.

In Reaction schemata (H), (K), (M), (V) and (W), $R^{21}$ and $R^{25}$ each are a $C_{1-6}$ alkyl group, and $R^{23}$ is a $C_{1-6}$ alkyl group, a $C_{1-6}$ alkoxy group, a $C_{6-14}$ aryl group or a mono- or di-$C_{1-4}$ alkylamino group.

In Reaction schemata (J) and (L), $R^{22}$ is H, a $C_{1-6}$ alkyl group or a hydroxyl group.

In Reaction schemata (D) and (R), $M^{k+}$ is a positive metal ion of k valence. As $M^{k+}$, for example, $Na^+$, $K^+$, $Mg^{2+}$, etc. are used.

In Reaction schema (D), (T) and (U), Rf is a $C_{1-6}$ perfluoroalkyl group.

In Reaction schema (A), the starting compound [II] can be produced according to a known method described in the literature (e.g. Japanese Unexamined Patent Publication No. 316771/1988) or the modified methods. The compound [IV] can be produced by reacting the compound [II] with amines represented by the compound [III].

The present reaction can be carried out, for example, according to the method described in "Comprehensive Organic Chemistry", Pergamon Press (1979), page 543 or the modified methods.

The amines [III] used in the present reaction are used for the reaction as it is or in the form of a salt with an acid as described hereinafter. The amount of the amines [III] used is not specifically limited and a large excess amount of them may be used as a solvent. Preferably, it is about 0.8 to 5 equivalents.

Good results are sometimes obtained by using an acid or base during the reaction or before or after the reaction for the purpose of accelerating the reaction and reducing by-products. As an acid catalyst, for example, there can be used inorganic protonic acid such as hydrochloric acid, hydrogen bromide, hydrogen iodide, phosphoric acid, sulfuric acid and the like; organic protonic acid such as formic acid, acetic acid, tartaric acid, malic acid, citric acid, oxalic acid, succinic acid, benzoic acid, trifluoroacetic acid, p-toluenesulfonic acid and the like; and Lewis acid such as aluminum chloride, ferric chloride, zinc chloride, titanium tetrachloride, boron trifluoride and the like. The amount of the acid catalyst used in the reaction is not specifically limited unless the reaction is adversely affected, and is preferably about 0.1 to 2.5 equivalents.

Examples of the base used as the catalyst include organic bases such as alcoholates of alkaline metal (e.g. sodium ethylate, sodium methylate, potassium tert-butoxide, etc.), amines (e.g. triethylamine, diisopropylethylamine, pyridine, N,N-dimethylaniline, etc.), and inorganic bases such as potassium carbonate, sodium carbonate, sodium hydroxide, potassium hydroxide, sodium hydrogencarbonate, potassium hydrogencarbonate, sodium hydride, etc. An amount of the base is not specifically limited unless the reaction is adversely affected. For example, a large excess amount can be also used as the case of pyridine which also serves as a solvent.

The present reaction can be carried out using a suitable solvent. Such a solvent is not specifically limited unless it reacts with a substrate, a reagent and a product to give by-products. The solvent which dissolves both substrate and reagent is preferred. As the solvent, for example, there can be used aliphatic hydrocarbons such as pentane, hexane, heptane, petroleum ether, etc.; aromatic hydrocarbons such as benzene, toluene, xylene, etc.; esters such as methyl acetate, ethyl acetate, ethyl formate, ethyl propionate, etc.; ketones such as acetone, methyl ethyl ketone, etc.; ethers such as diethyl ether, dipropyl ether, diisopropyl ether, dibutyl ether, tetrahydrofuran, dioxane, etc.; nitriles such as acetonitrile, propionitrile, etc.; acid amides such as dimethylformamide, dimethylacetamide, etc.; sulfoxides such as dimethyl sulfoxide, etc.; sulfones such as sulfolane, etc.; phosphoric acid amides such as hexamethylphosphoramide, etc.; halogenated hydrocarbons such as dichloromethane, chloroform, 1,2-dichloroethane, carbon tetrachloride, etc.; aromatic amines such as pyridine, picoline, lutidine, quinoline, etc.; a mixed solvent thereof; water; and a mixed solvent of these solvents and water.

The temperature used for the reaction is usually about −50 to 200° C., preferably about −30 to 150° C. The reaction time is usually about 0.1 to 72 hours, preferably about 0.1 to 24 hours.

The resulting compound may be supplied to the subsequent reaction after isolating and purifying by a known method per se such as concentration, concentration under reduced pressure, conversion of liquid properties, solvent change, extraction with solvent, distillation, crystallization, recrystallization, chromatography, etc., or supplied it as the reaction mixture.

In Reaction schema (B), the starting compound of the formula [V] can be produced according to the above reaction schema (A).

The compounds [VII] and [VIII] can be produced by reacting the compound [V] with an orthoacid ester of the formula [VI]. According to the present reaction, a product is obtained as any one of the compound [VII] or [VIII] or a mixture of both compounds according to the kind of the substrate [V] used, reaction condition, etc.

The present reaction can be carried out according to the method described in "Comprehensive Heterocyclic Chemistry", Pergamon Press (1985), page 108 or the modified methods.

The amount of the orthoacid ester [VI] used in the present reaction is not specifically limited, and a large excess amount can be used as the solvent. The present reaction can also be carried out in the absence of a catalyst, but is preferably carried out in the presence of a suitable acid catalyst. The kinds and amount of the acid catalyst are the same as those for the reaction of Reaction schema (A).

In Reaction schema (C), the reaction of [IX]→[XI] can be carried out, for example, according to the method described in "The Chemistry of the Sulfenic Acids and their Derivatives", John Wiley & Sons (1990), Chapter 10 or the modified methods.

The amount of the sulfenylhalide [X] used in the present reaction is not specifically limited, and is preferably about 0.8 to 2.5 equivalents. Good results are sometimes obtained by using a base during the reaction or before or after the reaction for the purpose of accelerating the reaction and reducing by-products. The kinds and amount of the base are the same as those for the reaction of Reaction schema (A).

The reaction of [XI]→[XII] can be carried out, for example, according to the method described in "Organic Functional Group Preparations", 2nd Edition, Academic Press (1983), Chapter 19 & Chapter 20 or the modified methods.

Examples of the oxidizing agent used in the present reaction include hydrogen peroxide, ozone, peracids (e.g. m-chloroperbenzoic acid), hydroperoxides (e.g. t-butylhydroperoxide), periodates (e.g. sodium periodate), halogens (e.g. chlorine, bromide), N-haloamides (imide) (e.g. N-bromoacetamide, N-cholorosuccinimide), etc. The amount of the oxidizing agent used in the present reaction is not specifically limited, and is preferably about 0.8 to 5 equivalents.

In Reaction schema (D), the reaction of [IX]→[XIV] can be carried out, for example, according to the method described in "The Chemistry of Cyanates and their Derivatives", Part 1, John Wiley & Sons (1977), Chapter 18 or the modified methods.

Examples of the halogenating agent used in the present reaction include chlorine, bromine, etc., preferably bromine. The amount of the compound [XIII] and the halogenating agent used in the present reaction is not specifically limited, and is preferably about 0.8 to 5 equivalents.

In the reaction of [XIV]→[XV], the disulfide [XV] can be obtained by the hydrolysis reaction of thiocyanate [XIV] and the automatic oxidation reaction of the resulting thiol.

The hydrolysis used in the present reaction can be carried out, for example, according to the known acidic hydrolysis, basic hydrolysis, neutral hydrolysis, etc. described in "Survey of Organic Syntheses" Vol.1 and Vol.2, Willey-Interscience (1970 and 1977), "SHIN JIKKENKAGAKU KOZA (New Expermental Chemistry Handbook)", Maruzen Publishing Co., Ltd., Tokyo, Vol. 14-III, Page 1363 (1978), etc.

Examples of the acid used in the present reaction include inorganic acids such as hydrochloric acid, hydrobromic acid, hydroiodic acid, phosphoric acid, sulfuric acid, etc.; and organic acids such as formic acid, acetic acid, trifluoroacetic acid, p-toluenesulfonic acid, etc.

Examples of the bases used in the present reaction include inorganic bases such as sodium hydrogen carbonate, potassium hydrogen carbonate, sodium carbonate, potassium carbonate, sodium hydroxide, potassium hydroxide, calcium hydroxide, phenyl lithium, butyl lithium, sodium hydride, potassium hydride, sodium methoxide, sodium ethoxide, metallic sodium, metallic potassium, etc.; and organic bases such as triethylamine, tributylamine, N,N-dimethylaniline, pyridine, lutidine, collidine, 4-(dimethylamino) pyridine, DBU (1,8-diazabicyclo[5.4.0]undecene-7), etc.

In the present reaction, automatic oxidation proceeds, together with the above hydrolysis reaction, without requiring any special operation. Good results are sometimes obtained by bubbling air or adding a weak oxidizing agent (e.g. iodine, etc.) for the purpose of accelerating the reaction.

The reaction of [XV]→[XVI] indicates a process of reacting the disulfide [XV] with the perfluoroalkylradical generator represented by RfX or $RfSO_2X^5$ in the presence of a radical initiator to produce the perfluoroalkyl sulfide [XVI].

Preferred examples of $RfX^4$ or $RfSO_2X^5$ used in the present reaction include $CF_3Br$, $CF_3CF_2Br$, $CF_3I$, $CF_3SO_2Cl$ and the like. An amount used is not specifically limited, and is preferably about 0.8 to 5 equivalents.

Preferred examples of the radical initiator used in the present reaction include organic radical generator such as benzoyl peroxide (BPO), azobisisobutyronitrile (AIBN), etc.; and inorganic radical generator such as $Na_2S_2O_4$, $SmI_2$, etc. The amount used is not specifically limited, and is preferably about 0.1 to 2.5 equivalents.

The reaction of [XVI]→[XII] can be carried out according to the methods corresponding the reaction of [XI]→[XII] in Reaction schema (C).

In Reaction schema (E), the reaction of [XVII]→[XIX] can be carried out, for example, according to the method described in "Organic Functional Group Preparations", 2nd Edition, Volume II, Academic Press (1986), Chapter 12 or the modified methods.

The starting compound [XVII] used in the present reaction can be produced, for example, according to the method described in the Japanese Unexamined Patent Publication No. 316771/1988, etc. or the modified methods.

The amount of the compound [XVII] used in the present reaction is not specifically limited, and is preferably about 0.8 to 2.5 equivalents.

In Reaction schema (F), the reaction of [XX]→[XXI] can be carried out, for example, according to the method described in "Organic Functional Group Preparations", 2nd Edition, Volume I, Academic Press (1983), Chapter 11 or the modified methods.

The starting compound [XX] used in the present reaction can be produced, for example, according to the method described in the Japanese Unexamined Patent Publication No. 316771/1988 etc. or the modified methods.

In the present reaction, R''' is H or the above-described group bonded through C. When R''' is H, the reaction are preferably carried out in the presence of a suitable condensing agent. As the dehydrating and condensing agent, for example, there can be used the known condensing agent such as dicyclohexylcarbodiimide, carbonyldiimidazole, thionyl chloride, etc.

The amount of the compound [XVIII] and the dehydrating and condensing agent used in the present reaction is not specifically limited, and is preferably about 0.8 to 2.5 equivalents.

The reaction of [XXI] [XXII] can be carried out, for example, according to the method described in "Reagents for Organic Synthesis", John Wiley & Sons (1967), Page 868 or "Comprehensive Organic Chemistry", Volume 2, Part 8, Pergamon Press (1979), Page 469, etc. or the modified methods.

The amount of triphenylphosphine or phosphorus pentachloride used in the present reaction is not specifically limited, and is preferably about 0.8 to 2.5 equivalents. The amount of carbon tetrachloride used in the present reaction is also not specifically limited, and is preferably 0.8 equivalents to a large excess amount. The carbon tetrachloride may be used as a solvent.

The reaction of [XXII]→[XXIV] can be carried out, for example, according to the method described in "Comprehensive Organic Chemistry", Volume 2, Part 8, Pergamon Press (1979), Page 474, etc. or the modified methods.

The amount of XH used in the present reaction is not specifically limited, and is preferably about 0.8 to 10 equivalents.

Good results are sometimes obtained by using a base during or before or after the reaction for the purpose of accelerating the reaction and reducing by-products. The kinds and amount of the base are the same as those for the reaction of Reaction schema (A).

In Reaction schema (G), the reaction of [XXV]→[XXVII] can be carried out, for example, according to the method described in "Protective Groups in Organic Synthesis", John Wiley & Sons (1981), Page 147 or the modified methods.

The amount of the compound [XXV] used in the present reaction is not specifically limited and a large excess amount of them may be used as a solvent. Preferably, it is about 0.8 to 10 equivalents.

The present reaction can also be carried out without a catalyst, but is preferably carried out in the presence of a suitable acid catalyst. The kinds and amount of the acid catalyst are the same as those for the reaction of Reaction schema (A).

The reactions of Reaction schemata (H) and (I) each can be carried out according to the similar or modified methods to Reaction schema (B).

In Reaction schema (J), the reaction of [XXVIII]→[XXX] can be carried out, for example, according to the method described in "Organic Functional Group Preparations", 2nd Edition, Volume III, Academic Press (1989), Chapter 6 or the modified methods.

The starting compound [XXVIII] can be prepared by the method described in Reaction schema (B) or (H).

The amines $R^{22}NH_2$ used in the present reaction are used for the reaction as it is or in the form of a salt with the acid as mentioned hereinafter. The amount of the amines $R^{22}NH_2$ used is not specifically limited and a large excess amount of them may be used as a solvent. Preferably, it is about 0.8 to 5 equivalents.

In Reaction schemata (K) and (L), the starting compounds [XXVIII] and [XXX] can be carried out according to the methods described in Reaction schema (H) and Reaction schema (J), respectively. The kinds and amount of the acid catalyst used in these reaction are the same as those for the reaction of Reaction schema (A).

In Reaction schema (M), the compound [XXXIII] can be prepared by reacting the compound [XXXII] with an acid anhydride of the formula: $(R^{23}CO)_2O$ wherein $R^{23}$ is as defined above or an acid chloride of the formula: $R^{23}COCl$ wherein $R^{23}$ is as defined above. The amount of the acid anhydride and acid chloride used in the present reaction is not specifically limited, and is preferably about 0.8 equivalents to a large excess amount. These may be used as a solvent.

Good results are sometimes obtained by using a base during the reaction or before or after the reaction for the purpose of accelerating the reaction and reducing by-products. The kinds and amount of the base are the same as those for the reaction of Reaction schema (A).

Reaction schema (N) is a process for producing the compound [XXXIV] by reacting the compound [XXV] with a phosgene (or an equivalent thereof such as diphosgene or triphosgene). The amount of the phosgene, diphosgene or triphosgene used in the present reaction is not specifically limited, and is preferably about 0.8 equivalents to a large excess amount. The disphosgen may be used as a solvent.

Good results are sometimes obtained by using a base during the reaction or before or after the reaction for the purpose of accelerating the reaction and reducing by-products. The kinds and amount of the base are the same as those for the reaction of Reaction schema (A).

The reaction of Reaction Schema (O) can be carried out, for example, according to the method described in "Comprehensive Organic Chemistry", Pergamon Press (1984), Vol. 5, §4.08, Page 471 or the modified methods.

The amount of the ethylenediamine used in the present reaction is not specifically limited, and a large excess amount of them may be used as a solvent.

The present reaction can also be carried out without a catalyst, but is preferably carried out in the presence of a suitable acid catalyst. The kinds and amount of the acid catalyst are the same as those for the reaction of Reaction schema (A).

In Reaction schema (P), the reaction of [XXXVI]→[XXXVII] can be carried out according to the similar or modified methods to those described in the reaction schema (A). When $R^{24}$ is H, the compound [XXXVII] and compound [XXXVIII] obtained in the present reaction are tautomers each other, as shown in the formula, and can take both structure of the compound [XXXVII] and [XXXVIII].

In Reaction schema (Q), the reaction of [XXXIX]→[XL] can be carried out according to the similar or modified methods to those described in Reaction schema (B). The reaction of [XL]→[XLI] can be carried out according to the acid hydrolysis described in Reaction schema (K).

The reactions of Reaction Schemata (R), (S), (T) and (U) can be carried out according to the method described in Reaction Schema (D).

The reducing agent used in the reaction of Reaction Schema (S) is not specifically limited. Preferably sodium borohydride is used for the reaction. The reactions of Reaction Schemata (V) and (W) can be carried out according to the methods described in Reaction Schemata (A) and (G), respectively.

The intermediate compounds [XXXVII], [XXXVIII], [XL], [XLI], [XLII] and [XLIII] are new compounds.

Each reaction of Reaction schemata (B) to (W) can be carried out using a suitable solvent. As the solvents are applicable the same ones as used for the reaction of Reaction schema (A).

The temperature used for each reaction in Reaction schemata (B) to (W) is usually about −50 to 200° C., preferably about −30 to 150° C. The reaction time is usually about 0.1 to 72 hours, preferably about 0.1 to 24 hours.

Each compound obtained according to Reaction schemata (B) to (W) may be supplied to the subsequent reaction after isolating or purifying by the same methods as used for the reaction of Reaction schema (A) or as the reaction mixture.

A salt of the compound [I] of the present invention may be any agrochemically acceptable salt. That is, when the compound [I] has an acid group such as a carboxyl group, a sulfo group, etc. in the molecule, the compound [I] may form a salt with a base. As the base, for example, there can be used inorganic bases such as alkali metal, e.g. sodium, potassium, lithium; alkaline earth metal, e.g. calcium, magnesium; ammonia and the like; and organic bases such as pyridine, collidine, triethylamine, triethanolamine and the like. There can also be used salts of inorganic acids such as hydrochloric acid, hydrobromic acid, hydroiodic acid, phosphoric acid, sulfuric acid, perchloric acid and the like; and salts of organic acids such as formic acid, acetic acid, tartaric acid, malic acid, citric acid, oxalic acid, succinic acid, benzoic acid, picric acid, methanesulfonic acid, p-toluenesulfonic acid and the like. The compound may form an intramolecular salt and the case is also included in the present invention.

The compound [I] and its salts are effective in preventing sanitary or horticultural insect pests and animal and plant parasites and can exert potent insecticidal activities when they are applied to harmed living animals or plants. Moreover, the compounds [I] and their salts possess safe and advantageous properties as agents for preventing sanitary, horitcultural or agricultural injurious insects, such as no substantial damage on plants and less toxicity against fishes.

The compound [I] or its salts can be used as an agricultural chemical, particularly, insecticide in any application form suited for general agricultural chemicals. That is, one, two, or more than two kinds of the compound [I] or its salts are used in the form of preparation such as emulsifiable concentrates, liquid preparation, flowable concentrates, micro emulsion, oil solution, wettable powders, dusts, granules, fine granules, seed coating, smoking pesticides, microcapsule, tablets, sprays, EW, ointments, poisonous bait or the like, according to the purpose of use, by dissolving or dispersing them in suitable liquid carriers or mixing them with or adsorbing them on suitable solid carriers. These formulations may contain, if necessary, emulsifying agent, suspending agent, spreading agent, penetrating agent, wetting agent, thickening agent, stabilizer, etc., and can be prepared by any conventional method known per se., e.g. mixing each ingredient.

Suitable examples of the liquid carriers, include solvents such as water, alcohols (for example, methanol, ethanol, n-propanol, iso-propanol or ethylene glycol), ketones (for example, acetone or methyl ethyl ketone), ethers (for example, dioxane, tetrahydrofuran, ethylene glycol monomethyl ether, diethylene glycol monomethyl ether or propylene glycol monomethyl ether), aliphatic hydrocarbons (for example, kerosine, kerosine oil, fuel oil or machine oil), aromatic hydrocarbons (for example, benzene, toluene, xylene, solvent naphtha or methylnaphthalene), halogenated hydrocarbons (for example, dichloromethane, chloroform or carbon tetrachloride), acid amides (for example, N,N-dimethylformamide or N,N-dimethylacetamide), esters (for example, ethyl acetate, butyl acetate or fatty acid glycerol ester) or nitriles (for example, acetonitrile or propionitrile). These solvents are used individually or as a suitable mixture of two, or more, of them.

Suitable examples of the solid carriers (diluents or dust carrier) include vegetable powder (for example, soy-been meal, tobacco meal, wheat flour or wood flour), mineral powders (for example, clays such as kaolin, bentonite, or acid clay, talcs such as talc powder or pyrophyllite powder), silicas (for example, diatomaceous earth or mica powder), aluminas, sulfur powder or activated charcoal. They are used individually or as a suitable mixture of two, more of them.

Also, suitable examples of bases for ointments include polyethylene glycol, pectin, polyalcohol esters of higher aliphatic acids (for example, glycerin mono-stearate), cellulose derivatives (for example, methyl cellulose), sodium alginate, bentonite, higher alcohols, polyalcohols (for example, glycerin), vaseline, white vaseline, liquid paraffin, lard, various vegetable oils, lanolin, dehydrates lanolin, hard oil or resins. These are used individually, or as a suitable mixture of two, or more, of them or together with surface active agents mentioned below.

As surface active agents used as the emulsifying agent, spreading agent, penetrating agent or dispersing agent, nonionic or anionic surface active agents such as soaps; polyoxyethylene alkyl aryl ethers (e.g., Noigen® and EA 142® from Dai-ichi Kogyo Seiyaku K.K., Japan, and Nonal® from Toho Chemical, Japan); alkyl sulfates (e.g., Emal 10® and Emal 40® from Kao K.K., Japan), alkyl sulfonates (e.g., Neogen® and Neogen T® from Dai-ichi Kogyo Seiyaku K.K., and Neopellex® from Kao K.K.); polyethylene glycol ethers (e.g., Nonipol 85®, Nonipol 100®, Nonipol 160® from Sanyo Kasei K.K., Japan); or polyhydric alcohol esters (e.g., Tween 20® and Tween 80® from Kao K.K.) are used, if necessary.

The compound [I] or its salts can also be used, as occasion demands, in combination with or as an admixture with other insecticides (for example, pyrethroid insecticides, organophosphorus insecticides, carbamate insecticides or natural insecticides), acaricides, nematicides, herbicides, plant hormones, plant growth regulators, fungicides (for example, copper fungicides, organic chloride fungicides, organic sulfur fungicides or phenolic fungicides), synergistic agents, attractants, repellents, pigments and/or fertilizers.

The amount of the compound [I] or a salt thereof contained in an insecticidal composition of the present invention is suitably about 0.1 to 80% by weight, preferably about 1 to 20% by weight, relative to the whole composition. For example, the amount is suitably about 1 to 80% by weight, preferably about 1 to 20% by weight in the case of emulsifiable concentrates, liquid preparations or wettable powders (e.g. granulated wettable powders), about 0.1 to 50% by weight, preferably about 0.1 to 20% by weight in the case of oil solution or dusts, about 5 to 50% by weight, preferably about 1 to 20% weight in the case of granules.

The other agricultural active ingredients (e.g. insecticide, herbicide, acaricide and/or fungicide) incorporated into the composition of the present invention may be used in an amount of about 1 to 80% by weight, preferably about 1 to 20% by weight, relative to the whole composition.

The amount of each of the additives other than the above-described active ingredients usually ranges, which varies depending on the variety and content of the agricultural active ingredient or the form of the composition, is usually about 0.001 to 99.9% by weight, preferably about 1 to 99% by weight, relative to the whole composition. More concretely, the surface active agent may be used in an amount of about 1 to 20% by weight, preferably about 1 to 15% by weight, the fluidizing agent an amount of about 1 to 20% by weight, and the carrier an amount of about 1 to 90% by weight, preferably about 1 to 70% by weight, relative to the whole composition. For example, the surface active agent may be used in an amount of about 1 to 20% by weight, preferably about 1 to 10% by weight and water may be used in rate of about 20 to 90% by weight in the case of liquid preparation. Emulsifiable concentrates, wettable powders (e.g. granulated wettable powders) or the like can be suitably diluted or extended (for example, to about 100 to 5,000 times) with water or the like, on the occasion of use, and then applied.

Typical examples of the insecticide, acaricide and fungicide which may be employed in admixture with the compound [I] or a salt thereof of the present invention will be given below: EPN, acephate, isoxathion, isofenphos, isoprocarb, etrimfos, oxydeprofos, quinalphos, cadusafos, chlorethoxyfos, chlorpyrifos, chlorpyrifos-methyl, chlorofenvinphos, salithion, cyanophos, disulfoton, dimethoate, sulprofos, diazinon, thiometon, tetrachlorvinphos, tebupirimfos, trichlorphon, nales, vamidothion, pyraclophos, pyridafenthion, pirimiphos-methyl, fenitrothion, fenthion, phenthoate, fosthiazate, butathiofos, prothiofos, propahos, profenofos, phosalone, malathion, methidathion, metolcarb, monocrotophos, BPMC, XMC, alanycarb, ethiofencarb, carbaryl, carbosulfan, carbofuran, xylylcarb, cloethocarb, thiodicarb, triazamate, pirimicarb, fenoxycarb, fenothiocarb, furathiocarb, propoxur, bendiocarb, benfuracarb, methomyl, acrinathrin, imiprothrin, ethofenprox, cycloprothrin, sigma-cypermethrin, cyhalothrin, cyfluthrin, cypermethrin, silafluofen, tefluthrin, deltamethrin, tralomethrin, fenvalerate, fenpropathrin, flucythrinate, fluvalinate, flufenoprox, fluproxygen, flumethrin, prallethrin, beta-cyfluthrin, benfluthrin, permethrin, acetamiprid, imidacloprid, cartap, thiocyclam, nitenpyram, bensultap, avermectin, emamectin-benzoate, clofentezine, chlorfluazuron, cyromazine, diafenthiuron, dienochlor, dichlorvos, diflubenzuron, spynosyn, sulfluramid, teflubenzuron, tebufenozide, tebufenpyrad, hydroprene, vaniliprole, pymetrozine, pyridaben, pyriproxyfen, pyrimidifen, fipronil, fenazaquin, fenpyroximate, fluazuron, flucycloxuron, flufenoxuron, buprofezin, hexaflumuron, hexythiazox, milbemycin, metoxadiazone, lufenuron, levamisol, AC-303, 630, NC-184, YI-5301, IBP, ampropylfos, edifenphos, chlorthiophos, tolclofos-methyl, fosetyl, ipconazole, imazalil, imibenconazole, etaconazole, epoxiconazole, cyproconazole, diniconazole, difenoconazole, tetraconazole, tebuconazole, triadimenol, triadimefon, triticonazole, triforine, bitertanol, viniconazole, fenarimol, fenbuconazole, fluotrimazole, furconazole-cis, flusilazole, flutriafol, bromuconazole, propiconazole, hexaconazole, pefurazoate, penconazole, myclobutanil, metconazole, cabendazin, debacarb, prothiocarb, benomyl, maneb, TPN, isoprothiolane, iprodione, iminoctadine-albesil, iminoctadine-triacetate, ethirimol, etridiazole, oxadixyl, oxycarboxin, oxolinic acid, ofurace, kasugamycin, carboxin, captan, clozylacon, chlobenthiazone, cyprodinil, cyprofuram, diethofencarb, dichlofluanid, diclomezine, zineb, dimethirimol, dimethomorph, dimefluazole, thiabendazole, thiophanate-methyl, thifluzamide, tecloftalam, triazoxide, triclamide, tricyclazole, tridemorph, triflumizole, validamycin A, hymexazol, pyracarbolid, pyrazophos, pyrifenox, pyrimethanil, pyroquilon, ferimzone, fenpiclonil, fenpropidin, fenpropimorph, fthalide, furametpyr, furalaxyl, fluazinam, furcarbanil, fluquinconazole, fludioxonil, flusulfamide, flutolanil, butiobate, prochloraz, procymidone, probenazole, benalaxyl, benodanil, pencycuron, myclozolin, metalaxyl, metsulfovax, methfuroxam, mepanipyrim, mepronil, kresoxim, azoxystrobin, SSF-126, carpropamid.

Specifically, the formulations containing the compound [I] or a salt thereof of the present invention are especially effective in preventing Hemiptera injurious insects such as *Eurydema rugosum, Scotinophara lurida, Riptortus clavatus, Stephanitis nashi, Laodelphax striatellus, Nilaparvata lugens, Nephotettix cincticeps, Unaspis yanonensis, Aphis glycines, Lipaphis erysimi, Brevicoryne brassicae, Aphis gossypii, Myzus persicae, Aulacorthum solani, Aphis spiraecola, Bemisia tabaci, Trialeurodes vaporariorum, Sogatella furcifera, Empoasca onukii, Pseudococcus comstocki, Planococcus citri, Icerya purchasi, Plautia stali, Eysarcoris parvus;* Lepidoptera injurious insects such as *Spodoptera litura, Plutella xylostella, Pieris rapae crucivora, Chilo suppressalis, Autographa nigrisigna, Helicoverpa assulta, Pseudaletia separate, Mamestra brassicae, Adoxophyes orana fasciata, Notarcha derogata, Cnaphalocrocis medinalis, Phthorimaea operculella, Chilo polychrysus, Tryporyza incertulas, Spodoptera exigua, Agrotis segetum, Agrotis ipsilon, Heliothis armigera, Heliothis virescens, Heliothis zea, Naranga aenescens, Ostrinia nubilalis, Ostrinia furnacalis, Parnara guttata, Adoxophyes sp., Caloptilia theivora, Phyllonorycter ringoneella, Carposina niponensis, Grapholita molesta;* Coleoptera injurious insects such as *Epilachna vigintioctopunctata, Aulacophora femoralis, Phyllotreta striplata, Oulema oryzae, Echinocnemus squameus, Lissorhoptrus oryzophilus, Anthonomus grandis, Callosobruchus chinensis, Sphenophorus venatus, Popillia iaponica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda;* Diptera injurious insects such as *Musca domestica, Culex pipiens pallens, Tabanus trigonus, Delia antiqua, Delia platura, Anopheles sinensis, Agromyza oryzae, Hydrellia griseola, Chlorops oryzae, Dacus cucurbitae, Ceratitis capitata, Liriomyza trifolii;* Orthoptera injurious insects such as *Locusta migratoria, Gryllotalpa africana, Oxya yezoensis, Oxya japonica;* Thysanoptera injurious insects such as *Thrips tabaci, Thrips parmi, Frankliniella occidentalis, Baliothrips biformis, Scirtothrips dorsalis;* Hymenoptera injurious insects such as *Athalia rosae;* Dictyoptera injurious insects such as *Blattella germanica, Periplaneta fuliginosa, Periplaneta japonica, Periplaneta americana;* Tetranychidaes such as *Tetranychus urticae, Panonychus citri, Tetranychus kanzawai, Tetranychus cinnabarinus, Panonychus ulmi, Aculops pelekassi, Polyphagotarsonemus latus, Rhizoglyphus echinopus;* and Nematodes such as *Aphelenchoides besseyi, Meloidogyne incognita, Pratylenchus penetrans, Nothotylenchus acris;* Termites such as *Coptotermes formosanus, Resticulitermes speratus, Odontotermes formosanus.*

The compound [I] or a salt thereof of the present invention can be used as excellent insecticidal composition having excellent insecticidal effects, fairly low toxicity and good safety. It can be used in a similar way to the conventional insecticidal composition and can exert more excellent effects in comparision with the conventional composition. For example, the insecticidal composition of the present invention can be applied to the target insects, by seed treatment, nursery box treatment, planting hole treatment, planting foot treatment, soil treatment, Foliar spray, smoking, drenching, water application in paddy field. The amount of application may broadly vary depending on the season, place and method of application, and so forth. In general, the active ingredient (the compound [I] or a salt thereof) is used in general, in an mount of 0.3 g to 3,000 g, preferably 50 g to 1,000 g per hectare. When the insecticidal composition of the present invention is in a wettable powder, it can be used by diluting it so as to be 0.1–1000 ppm, preferably 10–500 ppm as the final concentration of the active ingredient.

BEST MODE FOR CARRYING OUT OF THE INVENTION

This invention is illustrated in further detail in the Examples.

Elution in a column chromatography in the Referrence Examples and Examples was conducted while monitoring with TLC (Thin Layer Chromatography). In the TLC monitoring, the TLC plate used was Kieselgel® 60F$_{254}$ manufactured by Merck Co. (70–230 mesh), the developing solvent was the same as the one used for eluting in the column chromatography, and the detection was conducted with a UV detector. The silica gel for the column chromatography was Kieselgel 60 manufactured by Merck Co.

(70–230 mesh). NMR spectra indicate ¹H-NMR and were measured using tetramethylsilane as an internal standard with a spectrometer Varian EM390 (90 MHz) or Bruker AC-200P (200 MHz) and all δ values are expressed in ppm. The value shown in ( ) for a mixed solvent as the developing solvent is a mixing ratio in volume of constituent solvents. The abbreviations used in Examples, Reference Examples and Tables have the following meanings.

| | |
|---|---|
| Me | methyl group |
| Et | ethyl group |
| ph | phenyl group |
| s | singlet |
| br | broad |
| d | doublet |
| t | triplet |
| q | quartet |
| m | multiplet |
| dd | doublet of doublets |
| J | coupling constant |
| Hz | Hertz |
| DMSO-$d_6$ | deutero-dimethylsulfoxide |
| % | percentage by weight |
| m.p. | melting point |
| room temperature means 15–25° C. | |

Reference Example 1

5-Amino-1-(2,6-dichloro-4-trifluoromethylphenyl)-3- pyrazolecarboxamide oxime

5-Amino-3-cyano-1-(2,6-dichloro-4-trifluoromethylphenyl)pyrazole (10.0 g, 31.1 mmol) was dissolved in 150 ml of dry dioxane, and then hydroxylamine hydrochloride (3.35 g, 46.8 mmol) and triethylamine (6.6 ml, 47.4 mmol) were added with stirring at room temperature. The mixture was stirred at room temperature for 74 hours and the reaction solution was poured into 300 ml of iced water. The solution was stirred for 30 minutes and the deposited crystal was filtered. The resulting crystal was washed with water and then dried under reduced pressure to obtain 8.30 g (23.4 mmol) of the title compound as a colorless crystal. The aqueous layer obtained by combining the above filtrate and wash was extracted three times with 150 ml of ethyl acetate. The extracted solution was washed three times with 500 ml of an aqueous saturated sodium chloride solution and the organic layer was dried over anhydrous magnesium sulfate. After concentrating under reduced pressure, the resulting crystal was washed with 50 ml of chloroform-hexane (1:1) and then filtered to obtain 1.19 g (3.36 mmol) of the title compound as a pale brown crystal. Yield 86%.

m.p. 235–238° C. (dec.)

NMR(DMSO-$d_6$, δ) 5.28(2H,brs), 5.51(2H,brs), 5.55(1H, s), 8.12(2H,s), 9.51(1H,s)

Reference Example 2

1-(2,6-Dichloro-4-trifluoromethylphenyl)-5-methoxymethylideneamino-3-(1,2,4-oxadiazol-3-yl)pyrazole 5-Amino-1-(2,6-dichloro-4-trifluoromethylphenyl)-3-pyrazolecarboxamide oxime (4.00 g, 11.3 mmol) and triethyl orthoformate (2.45 g, 22.6 mmol) were dissolved in 40 ml of dry acetonitrile, and then p-toluenesulfonic acid monohydrate (0.02 g) was added with stirring at room temperature. After the mixture was stirred at 60° C. for 6 hours, the reaction mixture was cooled to room temperature. The reaction mixture was concentrated under reduced pressure and 50 ml of ethyl acetate was added to the concentrated residue. The organic layer was washed twice with 50 ml of an aqueous saturated sodium hydrogencarbonate solution, and then washed three times with 50 ml of an aqueous saturated sodium chloride solution. The organic layer was dried over anhydrous magnesium sulfate and then concentrated under reduced pressure. The resulting concentrated residue was subjected to silica gel column chromatography [eluent: mixed solvent of ethyl acetate and hexane (volume ratio=1:3)] to obtain 3.21 g (7.91 mmol) of the title compound as a pale yellow crystal.

Yield 70%.

m.p. 113–114° C.

NMR(CDCl$_3$, δ) 3.70(3H,s), 6.70(1H,s), 7.72(2H,s), 8.19 (1H,s), 8.82(1H,s)

Reference Example 3

5-Amino-1-(2,6-dichloro-4-trifluoromethylphenyl)-3-(1,2,4-oxadiazol-3-yl)pyrazole 1-(2,6-Dichloro-4-trifluoromethylphenyl)-5-methoxymethylideneamino-3-(1,2,4-oxadiazol-3-yl)pyrazole (2.80 g, 6.89 mmol) was dissolved in a mixed solvent of 50 ml of acetone and 5 ml of water, and then concentrated sulfuric acid (0.70 g, 6.92 mmol) was added with stirring at room temperature. The mixture was stirred at room temperature for 48 hours and the reaction solution was concentrated under reduced pressure. The pH of the residue was adjusted to about 8 by adding an aqueous saturated sodium hydrogencarbonate solution, followed by extracting three times with 30 ml of ethyl acetate. The organic layer was washed three times with 100 ml of water, dried over anhydrous magnesium sulfate and then concentrated under reduced pressure. The resulting concentrated residue was subjected to silica gel column chromatography [eluent: mixed solvent of ethyl acetate and hexane (volume ratio= 1:2)] to obtain 1.96 g (5.40 mmol) of the title compound as a colorless crystal.

Yield 78.1%.

m.p. 197–198° C.

NMR(CDCl$_3$, δ) 3.78(2H,brs), 6.30(1H,s), 7.76(2H,m), 8.77(1H,s)

Reference Example 4

5-Amino-1-(2,6-dichloro-4-trifluoromethylphenyl)-3-(1,2,4-oxadiazol-3-yl)-4-thiocyanato pyrazole Potassium thiocyanate (1.45 g, 14.9 mmol) was dissolved in 20 ml of dry methanol, and then a methanol (5 ml) solution of bromine (0.28 ml, 5.44 mmol) was added dropwise with stirring at −78° C. over 8 minutes (inner temperature: not higher than −65° C.). After the completion of adding dropwise, the mixture was stirred at −78° C. for 10 minutes and a methanol (15 ml) solution of 5-amino-1-(2, 6-dichloro-4-trifluoromethylphenyl)-3-(1,2,4-oxadiazol-3-yl)pyrazole (1.80 g, 4.94 mmol) was added dropwise over 15 minutes. The solution was stirred at −78° C. for 2 hours, warmed to room temperature and then stirred at the same temperature for 2 hours. The reaction mixture was poured into 100 ml of iced water. After stirring for 30 minutes, the deposited crystal was filtered. The resulting crystal was washed with water and then dried under reduced pressure to obtain 2.04 g (4.85 mmol) of the title compound as a colorless crystal. Yield 98.0%.

m.p. 195–198° C.

NMR(CDCl$_3$, δ) 4.50(2H,brs), 7.79(2H,m), 8.87(1H,s)

Reference Example 5

Bis{5-Amino-1-(2,6-dichloro-4-trifluoromethylphenyl)-3-(1,2,4-oxadiazol-3-yl)pyrazol-4-yl}disulfide 5-Amino-1-(2,6-dichloro-4-trifluoromethylphenyl)-3-(1,2,4-oxadiazol-3-yl)-4-thiocyanatopyrazole 1.00 g (2.37 mmol) was dissolved in 20 ml of dry methanol, and then 210 mg (5.00 mmol) of 90% sodium borohydride was added at 0° C. After the mixture was was stirred at 0° C. for 3.5 hrs, the reaction mixture was poured into 80 ml iced water, and then the precipitate was collected by filtration. After drying in vacuo, the resulting yellow crystal was recrystalized from ethyl acetate-n-hexane mixed solvent to obtain 512 mg (0.65 mmol) of the title compound as a yellow crystal. Yield 55%.

m.p. 226–228° C.

NMR(DMSO, δ) 6.18(4H,brs), 8.15(4H,s), 9.59(2H,s)

EXAMPLE 1

5-Amino-1-(2,6-dichloro-4-trifluoromethylphenyl)-4-methylsulfonyl-3-pyrazolecarboxamide oxime (Compound No. 1-2)

5-Amino-3-cyano-1-(2,6-dichloro-4-trifluoromethylphenyl)-4-methylsulfonylpyrazole (500 mg, 1.3 mmol) and hydroxylamine hydrochloride (87 mg, 1.3 mmol) were dissolved in 5 ml of dioxane, and then triethylamine (130 mg, 1.3 mmol) was added at room temperature. After the mixture was stirred at room temperature for 5 hours, the reaction mixture was poured into 100 ml of iced water and extracted with 100 ml of ethyl acetate. The extract was dried over anhydrous magnesium sulfate and then concentrated to obtain 470 mg (1.1 mmol) of the title compound as a pale pink crystal. Yield 87%.

m.p. 132–134° C.

NMR(CDCl$_3$, δ) 3.45(3H,s), 5.18(2H,br), 5.32(3H,br), 7.79(2H,s)

EXAMPLE 2

5-Amino-1-(2,6-dichloro-4-trifluoromethylphenyl)-4-trifluoromethylsulfinyl-3-pyrazolecarboxamide oxime (Compound No. 1-4)

5-Amino-3-cyano-1-(2,6-dichloro-4-trifluoromethylphenyl)-4-trifluoromethylsulfinylpyrazole (500 mg, 1.1 mmol) and hydroxylamine hydrochloride (79 mg, 1.1 mmol) were dissolved in 5 ml of dioxane, and then triethylamine (115 mg, 1.1 mmol) was added at room temperature. After the mixture was stirred at room temperature for 6 hours, hydroxylamine hydrochloride (79 mg, 1.1 mmol) and triethylamine (115 mg, 1.1 mmol) were further added, followed by stirring at room temperature for 2 hours. The reaction mixture was poured into 100 ml of iced water and extracted with 100 ml of ethyl acetate. The extract was dried over anhydrous magnesium sulfate and then concentrated to obtain a brown oily substance. This oily substance was subjected to silica gel column chromatography [eluent: mixed solvent of n-hexane and ethyl acetate (volume ratio= 3:1)] to obtain 340 mg (0.72 mmol) of the title compound as a colorless crystal. Yield 63%.

m.p. 203–205° C.

NMR(CDCl$_3$, δ) 5.03(2H,br), 5.20(2H,br), 7.34(1H,br), 7.82(2H,s)

EXAMPLE 3

5-Amino-1-(2,6-dichloro-4-trifluoromethylphenyl)-4-methylthio-3-pyrazolecarboxamide oxime (Compound No. 1-1)

5-Amino-3-cyano-1-(2,6-dichloro-4-trifluoromethylphenyl)-4-methylthiopyrazole (7.5 g, 20.4 mmol) and hydroxylamine hydrochloride (1.83 g, 25.5 mmol) were dissolved in 75 ml of dioxane, and then triethylamine (2.5 g, 24.5 mmol) was added at room temperature. After the mixture was stirred at room temperature for 29 hours, hydroxylamine hydrochloride (720 mg, 10.1 mmol) and triethylamine (1.0 g, 10.2 mmol) were further added, followed by stirring at room temperature for 22 hours. The reaction mixture was poured into 200 ml of iced water and extracted with 250 ml of ethyl acetate. The extract was dried over anhydrous magnesium sulfate and then concentrated to obtain a yellow crystal. The crystal was subjected to silica gel column chromatography [eluent: mixed solvent of n-hexane and chloroform (volume ratio= 1:1)] to obtain 6.98 g (17.4 mmol) of the title compound as a colorless crystal. Yield 85%.

m.p. 201–203° C.

NMR(DMSO-d$_6$, δ) 2.20(3H,s), 5.29(2H,br), 5.80(2H,br), 8.12(2H,s), 9.78(1H,s).

EXAMPLE 4

1-(2,6-Dichloro-4-trifluoromethylphenyl)-5-methoxymethylideneamino-4-methylthio-3-(1,2,4-oxadiazol-3-yl)pyrazole (Compound No. 2-1)

5-Amino-1-(2,6-dichloro-4-trifluoromethylphenyl)-4-methylthio-3-pyrazolecarboxamide oxime (1.77 g, 4.4 mmol) was dissolved in 25 ml of trimethyl orthoformate, and then p-toluenesulfonic acid monohydrate (130 mg) was added at room temperature. The mixture was heated. under reflux for 2 hours. The trimethyl orthoformate was distilled off under reduced pressure and the residue was dissolved in 60 ml of ethyl acetate. After the solution was washed with 120 ml of an aqueous saturated sodium chloride solution and dried over anhydrous magnesium sulfate, the solvent was distilled off to obtain a yellow crystal which was washed with n-hexane to yield 1.47 g (3.3 mmol) of the title compound as a pale yellow crystal. Yield 74%.

m.p. 119–121° C.

NMR(deutero-acetone, δ) 2.41(3H,s), 3.73(3H,s), 7.99 (2H,s), 8.67(1H,s), 9.42(1H,s)

EXAMPLE 5

5-Amino-1-(2,6-dichloro-4-trifluoromethylphenyl)-3-(N,N-dimethylamidino)-4-trifluoromethylsulfinylpyrazole (Compound No. 1-36)

5-Amino-3-cyano-1-(2,6-dichloro-4-trifluoromethylphenyl)-4-trifluoromethylsulfinylpyrazole (0.97 g, 2.22 mmol) was dissolved in 10 ml of 1,4-dioxane and dimethylamine (50% aqueous solution) (1.20 ml, 11.4 mmol) was added, and then the mixture was stirred at room temperature for 5 days. After stirring, 20 ml of water and 20 ml of an aqueous saturated sodium chloride solution were added and the solution was extracted twice with 30 ml of ethyl acetate. The extract was dried over anhydrous magnesium sulfate and the solvent was distilled off to obtain a yellow amorphous. The amorphous was subjected to silica gel column chromatography [eluent: mixed solvent of ethyl acetate and methanol (volume ratio=4:1)] and a small amount of ether was added to crystallize the resulting amorphous. This resultant was filtered to obtain 0.29 g (0.60 mmol) of the title compound as a colorless crystal. Yield 27%.

m.p. 123–126° C.

NMR(CDCl$_3$, δ) 3.01(6H,s), 5.21(3H,br), 7.80(2H,s)

EXAMPLE 6

5-Amino-1-(2,6-dichloro-4-trifluoromethylphenyl)-3-(N-hydroxy-N-methylamidino)-4-trifluoromethylsulfinylpyrazole (Compound No. 1-37)

5-Amino-3-cyano-1-(2,6-dichloro-4-trifluoromethylphenyl)-4-trifluoromethylsulfinylpyrazol e (1.00 g, 2.29 mmol) was dissolved in 10 ml of 1,4-dioxane and N-methylhydroxylamine hydrochloride (0.38 g, 4.55 mmol) and triethylamine (0.65 ml, 4.68 mmol) were added, and then the mixture was stirred at room temperature for 3 hours. After 30 ml of water, 60 ml of ethyl acetate and 30 ml of an aqueous saturated sodium chloride solution were added, the reaction mixture was shaken and the ethyl acetate layer was taken. The ethyl acetate layer was washed twice with 50 ml of water and dried over anhydrous magnesium sulfate and the solvent was distilled off to obtain a crystal. This crystal was washed with chloroform and then recrystallized from ethanol-hexane to obtain 0.59 g (1.22 mmol) of the title compound as a colorless crystal. Yield 53%.

m.p. 187–191° C.

NMR(DMSO-d$_6$, δ) 3.38(3H,s), 6.90–7.00(4H,br), 8.21 (2H,s)

EXAMPLE 7

1-(2,6-dichloro-4-trifluoromethylphenyl)-5-methoxymethylideneamino-3-(1,2,4-oxadiazol-3-yl)-4-trifluoromethylsulfinylpyrazole (Compound No. 2-15)

5-Amino-1-(2,6-dichloro-4-trifluoromethylphenyl)-4-trifluoromethylsulfinyl-3-pyrazolecarboxamide oxime (1.81 g, 3.85 mmol) was dissolved in 25 ml of trimethyl orthoformate and p-toluenesulfonic acid monohydrate (0.08 g) was added, and then the mixture was heated under reflux for 6 hours. After heating, trimethyl orthoformate was distilled off and 80 ml of ethyl acetate was added to the residue. The ethyl acetate layer was washed three times with 50 ml of an aqueous saturated sodium hydrogencarbonate solution, and then washed with 50 ml of an aqueous saturated sodium chloride solution. After drying over anhydrous magnesium sulfate, the solvent was distilled off to obtain a colorless oil. The oil was subjected to silica gel column chromatography [eluent: mixed solvent of ethyl acetate and chloroform (volume ratio=1:20)] and the resulting crystal was washed with hexane to obtain 1.03 g (1.97 mmol) of the title compound as a colorless crystal. Yield 51%.

m.p. 137–139° C.

NMR(CDCl$_3$, δ) 3.71(3H,s), 7.76(2H,m), 8.62(1H,s), 8.87(1H,s)

EXAMPLE 8

5-Amino-1-(2,6-dichloro-4-trifluoromethylphenyl)-4-trifluoromethylsulfonyl-3-pyrazolecarboxamide oxime (Compound No. 1-29)

5-Amino-3-cyano-1-(2,6-dichloro-4-trifluoromethylphenyl)-4-trifluoromethylsulfonylpyrazole (0.86 g, 1.90 mmol) was dissolved in 10 ml of 1,4-dioxane and hydroxylamine hydrochloride (0.22 g, 3.17 mmol) and triethylamine (0.45 ml, 3.24 mmol) were added, and then the mixture was stirred at room temperature. Ten hours after stirring, hydroxyamine hydrochloride (0.08 g, 1.2 mmol) and triethylamine (0.14 ml, 1.01 mmol) were further added. After the completion of adding, the solution was stirred at room temperature for 23 hours. Thirty milliliters of water and 15 ml of an aqueous saturated sodium chloride solution were added and then the reaction mixture was extracted twice with 30 ml of ethyl acetate. The ethyl acetate layer was washed with 20 ml of an aqueous saturated sodium chloride solution and dried over anhydrous magnesium sulfate. The solvent was distilled off to obtain a colorless crystal. This crystal was washed with a hexane-ethyl acetate mixed solvent (volume ratio=1:1) to obtain 0.82 g (1.68 mmol) of the title compound as a colorless crystal. Yield 89%.

m.p. 205–206° C.

NMR(DMSO-d$_6$, δ) 5.51(2H,br), 7.28(2H,br), 8.22(2H, s), 9.91(1H,s)

EXAMPLE 9

5-Amino-1-(2,6-dichloro-4-trifluoromethylphenyl)-3-(1,2,4-oxadiazol-3-yl)-4-trifluoromethylsulfonylpyrazole (Compound No. 2-7)

5-Amino-1-(2,6-dichloro-4-trifluoromethylphenyl)-4-trifluoromethylsulfonyl-3-pyrazolecarboxamide oxime (0.51 g, 1.87 mmol) was dissolved in 12 ml of trimethyl orthoformate and p-toluenesulfonic acid monohydrate (0.05 g) was added, and then the mixture was heated under reflux for 1 hour. Trimethyl orthoformate was distilled off and 80 ml of ethyl acetate was added to the residue. The ethyl acetate layer was washed twice with 50 ml of an aqueous saturated sodium hydrogencarbonate solution, and then washed once with 50 ml of an aqueous saturated sodium chloride solution. After drying over anhydrous magnesium sulfate, the solvent was distilled off to obtain a colorless crystal. This crystal was washed with a hexane-chloroform mixed solvent (volume ratio=2:1) to obtain 0.86 g (1.73 mmol) of the title compound as a colorless crystal. Yield 93%.

m.p. 205–208° C.

NMR(DMSO-d$_6$, δ) 7.66(2H,br), 8.26(2H,s), 9.82(1H,s)

EXAMPLE 10

1-(2,6-Dichloro-4-trifluoromethylphenyl)-5-methoxymethylideneamino-3-(1,2,4-oxadiazol-3-yl)-4-trifluoromethylsulfonylpyrazole (Compound No. 2-16)

To 5-amino-1-(2,6-dichloro-4-trifluoromethylphenyl)-3-(1,2,4-oxadiazol-3-yl)-4-trifluoromethylsulfonylpyrazole (1.00 g, 2.02 mmol) and 10 ml of trimethyl orthoformate was added p-toluenesulfonic acid monohydrate (0.05 g) with stirring at room temperature. The mixture was stirred with heating at reflux for 59 hours. The reaction mixture was cooled to room temperature and then concentrated under reduced pressure. The residue was dissolved in 50 ml of toluene and then concentrated under reduced pressure. After this procedure was repeated once again, the resulting concentrated residue was purified by subjecting to silica gel column chromatography [eluent: mixed solvent of ethyl acetate and chloroform (volume ratio=1:20)]. The resulting crystal was washed with hexane and filtered to obtain 124 mg (0.46 mmol) of the title compound as a colorless crystal. Yield 23.0%.

m.p. 157.5–158.5° C.

NMR(CDCl$_3$, δ) 3.79(3H,d,J=0.7 Hz), 7.77(2H,m), 8.12 (2H,m), 8.89(1H,s)

EXAMPLE 11

1-(2,6-Dichloro-4-trifluoromethylphenyl)-5-dimethylaminomethylideneamino-3-(1,2,4-oxadiazol-3-yl)-4-trifluoromethylsulfinylpyrazole (Compound No. 2-19)

5-Amino-1-(2,6-dichloro-4-trifluoromethylphenyl)-3-(1,2,4-oxadiazol-3-yl)-4-trifluoromethylsulfinylpyraz ole (500 mg, 1.04 mmol) and N,N-dimethylformamide dimethylacetal (90%) (280 mg, 2.12 mmol) were suspended in 20 ml of dry toluene. The resulting suspension was stirred with heating under reflux for 5 hours. The reaction mixture was cooled to room temperature and then concentrated under reduced pressure. The residue was dissolved in 50 ml of toluene and then concentrated again under reduced pressure. The resulting concentrated residue was purified by subjecting to silica gel preparative TLC [developing solvent: mixed solvent of hexane and ethyl acetate (volume ratio=3:1)] to obtain 350 mg (0.65 mmol) of the title compound as a colorless crystal. Yield 62.5%.

m.p. 140–140.5° C.

NMR(CDCl$_3$, δ) 2.81(3H,s), 3.10(3H,S), 7.68–7.75(2H, m), 8.65(1H,brs), 8.84(1H,s)

EXAMPLE 12

3-(N-Acetoxyamidino)-5-amino-1-(2,6-dichloro-4-trifluoromethylphenyl)-4-trifluoromethylsulfinylpyrazole (Compound No. 1-12)

5-Amino-1-(2,6-dichloro-4-trifluoromethylphenyl)-4-trifluoromethylsulfinyl-3-pyrazolecarboxamide oxime (0.50 g, 1.06 mmol) was dissolved in 8 ml of dichloroethane, and then pyridine (0.10 ml, 1.2 mmol) was added and acetyl chloride (99 mg, 1.26 mmol) dissolved in 2 ml of dichloroethane was added dropwise at room temperature. After the completion of adding dropwise, the mixture was stirred at room temperature for 2 hours and the solvent was distilled off. To the resulting mixture, 50 ml of ethyl acetate was added, then 15 ml of water and 15 ml of an aqueous saturated sodium chloride solution was added. The ethyl acetate layer was taken and washed once with 30 ml of 0.5 N hydrochloric acid, then washed three times with 30 ml of an aqueous saturated sodium chloride solution. After drying over anhydrous magnesium sulfate, the solvent was distilled off to obtain 0.54 g (1.06 mmol) of the title compound as a colorless amorphous. Yield 99%.

NMR(DMSO-d$_6$, δ) 2.13(3H,s), 6.74(4H,br), 8.20(2H,s)

EXAMPLE 13

5-Amino-1-(2,6-dichloro-4-trifluoromethylphenyl)-3-(5-oxo-4H-1,2,4-oxadiazolin-3-yl)-4-trifluoromethylsulfinylpyrazole (Compound No. 4-1)

5-Amino-1-(2,6-dichloro-4-trifluoromethylphenyl)-4-trifluoromethylsulfinyl-3-pyrazolecarboxamide oxime (0.78 g, 1.66 mmol) was dissolved in 20 ml of toluene and 10 ml of THF, and then triphosgene (0.25 g, 0.84 mmol) was added. The mixture was stirred at room temperature for 4 hours and, after the completion of the reaction, 50 ml of ethyl acetate was added. The reaction solution was washed three times with 30 ml of an aqueous sodium hydrogencarbonate solution and then washed twice with 30 ml of an aqueous saturated sodium chloride solution. After drying over anhydrous magnesium sulfate, the solvent was distilled off to obtain a yellow amorphous. The amorphous was subjected to silica gel column chromatography [eluent: mixed solvent of ethyl acetate and chloroform (volume ratio=1:1)] and the resulting amorphous was crystallized by adding chloroform. The resulting crystal was washed with a mixed solvent of chloroform and ethyl acetate (=10:1) to obtain 304 mg (0.61 mmol) of the title compound as a colorless crystal. Yield 37%.

m.p. 270–273° C. (dec.)

NMR(DMSO-d$_6$, δ) 7.06(2H,br), 8.22(2H,s), 13.22(1H, br)

EXAMPLE 14

1-(2,6-Dichloro-4-trifluoromethylphenyl)-5-hydroxyaminomethylideneamino-3-(1,2,4-oxadiazol-3-yl) -4-trifluoromethylsulfinylpyrazole (Compound No. 2-14)

To 1-(2,6-dichloro-4-trifluoromethylphenyl)-5-methoxymethylideneamino-3-(1,2,4-oxadiazol-3-yl)-4-trifluoromethylsulfinylpyrazole (720 mg, 1.38 mmol) were added hydroxylamine hydrochloride (240 mg, 3.45 mmol), dioxane (2.0 ml) and triethylamine (0.40 ml, 2.90 mmol), and then the mixture was stirred at room temperature. Five hours after stirring, triethylamine (0.4 ml, 2.90 mmol) and dioxane (1.0 ml) were further added, followed by stirring at room temperature for 66 hours. After 40 ml of ethyl acetate was added, the organic layer was washed three times with 30 ml of an aqueous saturated sodium chloride solution. After drying over anhydrous magnesium sulfate, the solvent was distilled off to obtain a pale yellow oil. The oil was purified by subjecting to silica gel preparative TLC [developing solvent: mixed solvent of chloroform and ethyl acetate (volume ratio=10:1)] to obtain 284 mg (0.54 mmol) of the title compound as a colorless crystal. Yield 55%.

m.p. 112–114° C.

NMR(CD$_3$CN, δ) 6.57(1H,br), 8.02–8.05(2H,m), 8.60 (1H,br), 9.14(1H,s), 9.20(1H,br)

EXAMPLE 15

1-(2,6-Dichloro-4-trifluoromethylphenyl)-5-formylamino-3-(1,2,4-oxadiazol-3-yl)-4-trifluoromethylsulfinylpyrazole (Compound No. 2-21)

1-(2,6-Dichloro-4-trifluoromethylphenyl)-5-hydroxyaminomethylideneamino-3-(1,2,4-oxadiazol-3-yl)-4-trifluoromethylsulfinylpyrazole (3.50 g, 6.69 mmol) was dissolved in 30 ml of acetone and 1.2 N hydrochloric acid (12 ml, 14.4 mmol) was added, and then the mixture was stirred at room temperature for 3 days. After 20 ml of water was added, the reaction mixture was neutralized with sodium hydrogencarbonate (powder). The solvent was distilled off and 20 ml of water and 100 ml of ethyl acetate were added, followed by partitioning. The aqueous layer was extracted with 30 ml of ethyl acetate and combined with the ethyl acetate layer, followed by washing with 50 ml of an aqueous saturated sodium hydrogencarbonate solution, then with 50 ml of an aqueous saturated sodium chloride solution. After drying over anhydrous magnesium sulfate, the solvent was distilled off to obtain a colorless amorphous. The amorphous was subjected to silica gel column chromatography [eluent: mixed solvent of ethyl acetate and chloroform (volume ratio=1:10)] to obtain 453 mg (0.89 mmol) of the title compound as a colorless crystal. Yield 13%.

m.p. 182–184° C.

NMR(CD$_3$CN, δ) 7.94(1H,s), 7.97(1H,s), 8.14(1H,br), 9.00(1H,br), 9.16(1H,s)

At the same time, 5-amino-1-(2,6-dichloro-4-trifluoromethylphenyl)-3-(1,2,4-oxadiazol-3-yl)-4-trifluoromethylsulfinylpyrazole (1.98 g, 4.12 mmol) was obtained by the reaction. Yield 62%.

m.p. 200–202° C.

NMR(DMSO-d$_6$, δ) 6.98(2H,br), 8.23(2H,s), 9.79(1H,br)

EXAMPLE 16

5-Amino-1-(2,6-dichloro-4-trifluoromethylphenyl)-3-(1,2,4-oxadiazol-3-yl)-4-trifluoromethylsulfinylpyrazole (Compound No. 2-2)

1-(2,6-Dichloro-4-trifluoromethylphenyl)-5-methoxymethylideneamino-3-(1,2,4-oxadiazol-3-yl)-4-trifluoromethylsulfinylpyrazole (151 mg, 0.29 mmol) was dissolved in 5 ml of acetone and 1.2 N hydrochloric acid (0.12 ml, 0.14 mmol) was added, and then the mixture was stirred at room temperature. Seven hours after stirring, 1.2 N hydrochloric acid (0.12 ml, 0.14 mmol) was further added, followed by stirring at room temperature for 3 days. Furthermore, 1.2 N hydrochloric acid (0.12 ml, 0.14 mmol) was added, followed by heating to 50° C. and stirring for another 9 hours. After 5 ml of water and 2 ml of an aqueous saturated sodium hydrogencarbonate solution were added, acetone was distilled off and extracted with 40 ml ethyl acetate. The ethyl acetate layer was washed twice with 30 ml of an aqueous saturated sodium chloride solution and dried over anhydrous magnesium sulfate. The solvent was distilled off to obtain 136 mg (0.29 mmol) of the title compound as a yellowish crystal.

m.p. 200–202° C.

NMR(DMSO-d$_6$, δ) 6.98(2H,br), 8.23(2H,s), 9.79(1H,br)

EXAMPLE 17

5-Amino-1-(2,6-dichloro-4-trifluoromethylphenyl)-3-(4H-1,2,4-oxadiazolin-3-yl)-4-trifluoromethylsulfinylpyrazole (Compound No. 3-5)

5-Amino-1-(2,6-dichloro-4-trifluoromethylphenyl)-4-trifluoromethylsulfinyl-3-pyrazolecarboxamide oxime (1.00 g, 2.13 mmol) was dissolved in 10 ml of acetonitrile and an aqueous formaldehyde solution (37%) (0.80 ml, 10.7 mmol) and five drops of acetic acid were added, and then the mixture was heated to 50° C. and stirred for 9 hours. Then, 3 ml of acetonitrile, an aqueous formaldehyde solution (37% aq.) (0.80 ml, 10.7 mmol) and three drops of acetic acid were further added, followed by refluxing for 10 hours. The solvent was distilled off and 50 ml of ethyl acetate was added to the residue. The solution was washed twice with 30 ml of an aqueous saturated sodium chloride solution, twice with an aqueous saturated sodium hydrogencarbonate solution and then twice with 30 ml of an aqueous saturated sodium chloride solution. After drying over anhydrous magnesium sulfate, the solvent was distilled off to obtain a colorless amorphous. The amorphous was subjected to silica gel column chromatography [eluent: mixed solvent of ethyl acetate and hexane (volume ratio=1:2)] and the resulting crystal was washed with a mixed solvent of hexane and chloroform (volume ratio=10:1) to obtain 0.41 g (0.85 mmol) of the title compound as a colorless crystal. Yield 40%.

m.p. 126–130° C.

NMR(CDCl$_3$, δ) 5.01(1H,br), 5.19(2H,br), 5.43(1H,s), 5.47(1H,s), 7.82(2H,s)

EXAMPLE 18

5-Amino-1-(2,6-dichloro-4-trifluoromethylphenyl)-3-(2-imidazolin-2-yl)-4-trifluoromethylsulfinylpyrazole (Compound No. 3-1)

5-Amino-3-cyano-1-(2,6-dichloro-4-trifluoromethylphenyl)-4-trifluoromethylsulfinyl-pyrazole (0.81 g, 1.85 mmol) was dissolved in 8 ml of THF, and then ethylenediamine (0.40 ml, 5.98 mmol) was added. The mixture was stirred at room temperature for 1 hour, heated to 50° C. and then stirred for 24 hours. Then, ethylenediamine (0.40 ml, 5.98 mmol) and THF (3 ml) were further added, followed by stirring for 14 hours. After the completion of the reaction, 20 ml of water was added and THF was distilled off and, further, 10 ml of water and 20 ml of an aqueous saturated sodium chloride solution were added. The mixture was extracted twice with 40 ml of ethyl acetate and the ethyl acetate layer was washed twice with 30 ml of an aqueous saturated sodium chloride solution. The resultant was dried over anhydrous magnesium sulfate and then concentrated to obtain a yellow amorphous. The amorphous was subjected to silica gel column chromatography [eluent: mixed solvent of ethyl acetate and hexane (volume ratio=1:2)] to obtain 0.34 g (0.71 mmol) of the title compound as a pale yellow amorphous. Yield 38%.

NMR(CDCl$_3$, δ) 3.75(4H,br), 5.22(3H,br), 7.80(2H,s)

EXAMPLE 19

5-Amino-1-(2,6-dichloro-4-trifluoromethylphenyl)-3-(2,5-dihydro-2-methyl-1,2,4-oxadiazol-3-yl)-4-trifluoromethylsulfinylpyrazole (Compound No. 5-11)

5-Amino-1-(2,6-dichloro-4-trifluoromethylphenyl)-3-(N-hydroxy-N-methylamidino)-4-trifluoromethylsulfinylpyrazole (1.00 g, 2.07 mmol) was dissolved in 10 ml of acetonitrile, and then aqueous 37% formaldehyde solution 840 mg (10.3 mmol) and 5 drops of acetic acid were added. After the mixture was stirred at 50° C. for 5 hours, aqueous 37% formaldehyde solution 840 mg (10.3 mmol) and, 5 drops of acetic acid were further added, followed by stirring at 50° C. for 5 hours. The reaction mixture was concentrated in vacuo and to the residual oil was added ethyl acetate, and then washed twice with an aqueous saturated sodium hydrogencarbonate solution, once with an aqueous saturated sodium chloride solution. After drying over anhydrous magnesium sulfate, the solvent was distilled off. The resulting concentrated residue was purified by silica gel column chromatography [eluent: mixed solvent of ethyl acetate and n-hexane (volume ratio=1:2)] to obtain 260 mg (0.52 mmol) of the title compound as a colorless crystal. Yield 25%.

m.p. 165–167° C.

NMR(CDCl$_3$, δ) 3.31(3H,s), 5.20(2H,brs,), 5.66(2H,brs), 7.81(2H,s).

EXAMPLE 20

1-(2,6-dichloro-4-trifluoromethylphenyl)-5-dimethylamino-3-(1,2,4-oxadiazol-3-yl)-4-trifluoromethylsulfinylpyrazole (Compound No. 2-32)

1-(2,6-dichloro-4-trifluoromethylphenyl)-5-dimethylamino-4-trifluoromethylsulfinyl-3- pyrazolecarboxamide oxime 0.59 g (1.18 mmol) was dissolved in 5 ml of trimethyl orthoformate, and then 5 mg of p-toluenesulfonic acid monohydrate was added. After the mixture was was stirred at room temperature for 3 hrs, trimethyl orthoformate was distilled off in vacuo, and then added 40 ml of ethyl acetate. The ethyl acetate solution was washed twice with 15 ml of aqueous saturated sodium hydrogencarbonate solution, and then once with 15 ml of aqueous saturated sodium chloride solution. After drying over anhydrous magnesium sulfate, the solvent was distilled off to obtain 583 mg (1.15 mmol) of the title compound as a colorless crystal. Yield 97%.

m.p. 82–84° C.

NMR(CDCl$_3$, δ) 2.87(6H,s), 7.79(2H,s), 8.86(1H,s).

EXAMPLE 21

1-(2,6-dichloro-4-trifluoromethylphenyl)-5-methylamino-3-(1,2,4-oxadiazol-3-yl)-4-trifluoromethylsulfonylpyrazole (Compound No. 2-40)

1-(2,6-dichloro-4-trifluoromethylphenyl)-5-methylamino-4-trifluoromethylsulfonyl-3-pyrazolecarboxamide oxime 500 mg (1.00 mmol) was dissolved in 5 ml of trimethyl orthoformate, and then 5 mg of p-toluenesulfonic acid monohydrate was added. After the mixture was was stirred at room temperature for 6hrs, trimethyl orthoformate was distilled off in vacuo, and then added 20 ml of ethyl acetate. The ethyl acetate solution was washed once with 30 ml of aqueous saturated sodium hydrogencarbonate solution, and then four times with 30 ml of aqueous saturated sodium chloride solution. After drying over anhydrous magnesium sulfate, the solvent was distilled off. The resulting concentrated residue was purified by silica gel column chromatography [eluent: chloroform] to obtain 320 mg (0.63 mmol) of the title compound as a colorless crystal. Yield 63%.

m.p. 156.5–157.5° C.

NMR(CDCl$_3$, δ) 2.63(3H,d,J=5.5 Hz), 6.48(1H,q,J=5.5 Hz), 7.78(2H,s), 8.85(1H,s).

EXAMPLE 22

5-Amino-1-(2,6-dichloro-4-trifluromethylphenyl)-3-(1,2,4-oxadiazol-3-yl)-4-trifluoromethylthiopyrazole (Compound No. 2-12)

Bis{5-Amino-1-(2,6-dichloro-4-trifluoromethylphenyl)-3-(1,2,4-oxadiazol-3-yl)pyrazol-4-yl}disulfide 1.00 g (1.27 mmol), 10 ml of dry 1,4-dioxane, trifluoromethanesulfonylchloride 0.41 ml(3.85 mmol) and azobisisobutyronitrile 0.21 g (1.25 mmol) were placed in sealed tube, and then stirred at 120° C. for 7hrs. After the reaction mixture was cooled to room temperature, concentrated in vacuo, and then added 50 ml ethyl acetate. The mixture was washed with once with 50 ml of aqueous 1N hydrochloric acid solution, once with 50 ml of water, once with aqueous saturated sodium hydrogencarbonatesolution, and then three times with 30 ml of aqueous saturated sodium chloride solution. After drying over anhydrous magnesium sulfate, the solvent was distilled off. The resulting concentrated residue was purified by silica gel column chromatography [eluent: mixed solvent of ethyl acetate and n-hexane(volume ratio=1:2)] to obtain 83 mg (0.18 mmol) of the title compound as a red crystal. Yield 7%.

m.p. 190–192° C.

NMR(CDCl$_3$, δ) 4.42(2H,br), 7.79(2H,s), 8.83(1H,s).

Examples of the present compound obtained according to the same manner as that described in Examples 1 to 22 are shown in the following Tables 1 to 13, together with the compounds obtained in the above Examples.

TABLE 1

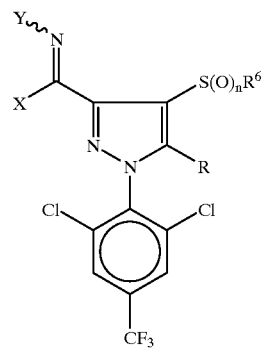

| Comp. No. | R$^6$ | R | X | Y | n | mp. (° C.) |
|---|---|---|---|---|---|---|
| 1-1 | Me | NH$_2$ | NH$_2$ | OH | 0 | 201–203 |
| 1-2 | Me | NH$_2$ | NH$_2$ | OH | 2 | 132–134 |
| 1-3 | Me | NH$_2$ | NH$_2$ | OMe | 2 | 194–196 |
| 1-4 | CF$_3$ | NH$_2$ | NH$_2$ | OH | 1 | 203–205 |
| 1-5 | CF$_3$ | NH$_2$ | NH$_2$ | NH$_2$ | 1 | |
| 1-6 | CF$_3$ | NH$_2$ | NH$_2$ | NHMe | 1 | |
| 1-7 | CF$_3$ | NH$_2$ | NH$_2$ | NMe$_2$ | 1 | |
| 1-8 | CF$_3$ | NH$_2$ | NH$_2$ | NHCOMe | 1 | |
| 1-9 | CF$_3$ | NH$_2$ | NH$_2$ | NMeCOMe | 1 | |
| 1-10 | CF$_3$ | NH$_2$ | NH$_2$ | NHCO$_2$Et | 1 | |
| 1-11 | CF$_3$ | NH$_2$ | NH$_2$ | OMe | 1 | 175–177 |
| 1-12 | CF$_3$ | NH$_2$ | NH$_2$ | OCOMe | 1 | (amorphous)[1)] |
| 1-13 | CF$_3$ | NH$_2$ | NHCOMe | OMe | 1 | |

TABLE 1-continued

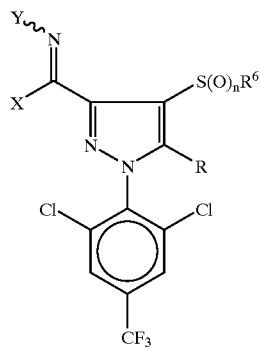

| Comp. No. | R⁶ | R | X | Y | n | mp. (° C.) |
|---|---|---|---|---|---|---|
| 1-14 | $CF_3$ | NHCOMe | NHCOMe | OMe | 1 | |
| 1-15 | $CF_3$ | $NH_2$ | NHMe | OMe | 1 | |
| 1-16 | $CF_3$ | NHMe | NHMe | OMe | 1 | |

[1]) NMR (DMSO, δ) 2.13 (3H, s), 6.74 (4H, br), 8.20 (2H, s)

TABLE 2

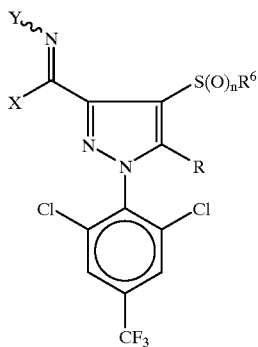

| Comp. No. | R⁶ | R | X | Y | n | mp. (° C.) |
|---|---|---|---|---|---|---|
| 1-17 | $CF_3$ | $NH_2$ | $NH_2$ | $NH_2$ | 2 | |
| 1-18 | $CF_3$ | $NH_2$ | $NH_2$ | NHMe | 2 | |
| 1-19 | $CF_3$ | $NH_2$ | $NH_2$ | $NMe_2$ | 2 | |
| 1-20 | $CF_3$ | $NH_2$ | $NH_2$ | NHCOMe | 2 | |
| 1-21 | $CF_3$ | $NH_2$ | $NH_2$ | NMeCOMe | 2 | |
| 1-22 | $CF_3$ | $NH_2$ | $NH_2$ | $NHCO_2Et$ | 2 | |
| 1-23 | $CF_3$ | $NH_2$ | $NH_2$ | OMe | 2 | |
| 1-24 | $CF_3$ | $NH_2$ | $NH_2$ | OCOMe | 2 | |
| 1-25 | $CF_3$ | $NH_2$ | NHCOMe | OMe | 2 | |
| 1-26 | $CF_3$ | NHCOMe | NHCOMe | OMe | 2 | |
| 1-27 | $CF_3$ | $NH_2$ | NHMe | OMe | 2 | |
| 1-28 | $CF_3$ | NHMe | NHMe | OMe | 2 | |
| 1-29 | $CF_3$ | $NH_2$ | $NH_2$ | OH | 2 | 205–206 |
| 1-30 | $CF_3$ | $NH_2$ | $NH_2$ | OH | 0 | 185–187 |
| 1-31 | $CF_3$ | $NH_2$ | $NH_2$ | $OCO_2Me$ | 1 | (amorphous)[2]) |

TABLE 2-continued

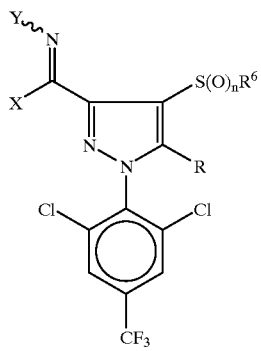

| Comp. No. | R⁶ | R | X | Y | n | mp. (° C.) |
|---|---|---|---|---|---|---|
| 1-32 | $CF_3$ | $NH_2$ | $NH_2$ | (─OCO─C₆H₄─$Bu^t$) | 1 | (amorphous)[3] |
| 1-33 | $CF_3$ | $NH_2$ | $NH_2$ | (─OCO─C₆H₅) | 1 | 137–141 |
| 1-34 | $CF_3$ | $NH_2$ | $NH_2$ | $OCH(OMe)_2$ | 1 | 175–177 |
| 1-35 | $CF_3$ | $NH_2$ | $NH_2$ | Me | 1 | 221–223 |
| 1-36 | $CF_3$ | $NH_2$ | $NMe_2$ | H | 1 | 123–126 |
| 1-37 | $CF_3$ | $NH_2$ | N(OH)Me | H | 1 | 187–191 |

[2]NMR (DMSO, δ) 3.79 (3H, s), 6.73 (4H, br), 8.20 (2H, s)
[3]NMR (DMSO, δ) 1.33 (9H, s), 6.74 (2H, br), 6.91 (2H, br), 7.52 (2H, d, J = 8.4 Hz), 8.14 (2H, d, J = 8.4 Hz), 8.19 (2H, s)

TABLE 3

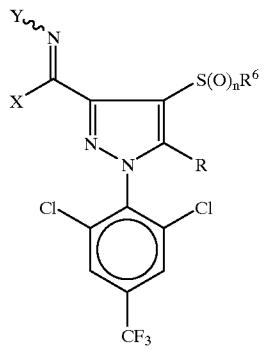

| Comp. No. | R⁶ | R | X | Y | n | mp. (° C.) |
|---|---|---|---|---|---|---|
| 1-38 | $CF_3$ | NHMe | $NH_2$ | OH | 0 | |
| 1-39 | $CF_3$ | $NMe_2$ | $NH_2$ | OH | 0 | 210–212 |
| 1-40 | $CF_3$ | NHEt | $NH_2$ | OH | 0 | 187–189 |
| 1-41 | $CF_3$ | $NEt_2$ | $NH_2$ | OH | 0 | 195–196 |
| 1-42 | $CF_3$ | $NHPr^n$ | $NH_2$ | OH | 0 | |
| 1-43 | $CF_3$ | $NPr_2^n$ | $NH_2$ | OH | 0 | |
| 1-44 | $CF_3$ | $NHPr^i$ | $NH_2$ | OH | 0 | |
| 1-45 | $CF_3$ | $NHCH_2Ph$ | $NH_2$ | OH | 0 | |
| 1-46 | $CF_3$ | $N(CH_2Ph)_2$ | $NH_2$ | OH | 0 | |
| 1-47 | $CF_3$ | $NH_2$ | $NH_2$ | OH | 1 | |
| 1-48 | $CF_3$ | NHMe | $NH_2$ | OH | 1 | |
| 1-49 | $CF_3$ | $NMe_2$ | $NH_2$ | OH | 1 | 158–160 |
| 1-50 | $CF_3$ | NHEt | $NH_2$ | OH | 1 | 185–187 |
| 1-51 | $CF_3$ | $NEt_2$ | $NH_2$ | OH | 1 | 175–177 |
| 1-52 | $CF_3$ | $NHPr^n$ | $NH_2$ | OH | 1 | |
| 1-53 | $CF_3$ | $NPr_2^n$ | $NH_2$ | OH | 1 | |
| 1-54 | $CF_3$ | $NHPr^i$ | $NH_2$ | OH | 1 | 199–200 |
| 1-55 | $CF_3$ | $NHCH_2Ph$ | $NH_2$ | OH | 1 | (amorphous)[11] |
| 1-56 | $CF_3$ | $N(CH_2Ph)_2$ | $NH_2$ | OH | 1 | 160–161 |
| 1-57 | $CF_3$ | $NH_2$ | $NH_2$ | OH | 2 | |
| 1-58 | $CF_3$ | NHMe | $NH_2$ | OH | 2 | 205–206 |
| 1-59 | $CF_3$ | $NMe_2$ | $NH_2$ | OH | 2 | 94–96 |
| 1-60 | $CF_3$ | NHEt | $NH_2$ | OH | 2 | 181–182 |

[11]NMR (CDCl₃, δ) 4.04 (2H, d, J = 4.5 Hz), 5.00 (2H, brs), 6.87–7.08 (3H, m), 7.12–7.37 (4H, m), 7.42–7.58 (2H, m)

TABLE 4

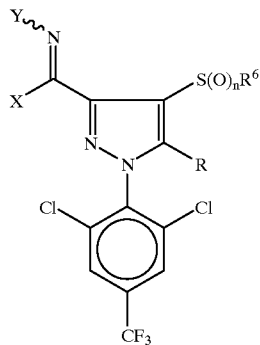

| Comp. No. | R⁶ | R | X | Y | n | mp. (° C.) |
|---|---|---|---|---|---|---|
| 1-61 | $CF_3$ | $NEt_2$ | $NH_2$ | OH | 2 | 89–91 |
| 1-62 | $CF_3$ | $NHPr^n$ | $NH_2$ | OH | 2 | |
| 1-63 | $CF_3$ | $NPr_2^n$ | $NH_2$ | OH | 2 | |
| 1-64 | $CF_3$ | $NHPr^i$ | $NH_2$ | OH | 2 | |
| 1-65 | $CF_3$ | $NHCH_2Ph$ | $NH_2$ | OH | 2 | |
| 1-66 | $CF_3$ | $N(CH_2Ph)_2$ | $NH_2$ | OH | 2 | |
| 1-67 | $CF_3$ | $NH_2$ | N(OH)Me | H | 0 | 165–166 |
| 1-68 | $CF_3$ | NHMe | N(OH)Me | H | 0 | |
| 1-69 | $CF_3$ | $NMe_2$ | N(OH)Me | H | 0 | 190–192 |
| 1-70 | $CF_3$ | NHEt | N(OH)Me | H | 0 | 127–128 |
| 1-71 | $CF_3$ | $NEt_2$ | N(OH)Me | H | 0 | 177–178 |
| 1-72 | $CF_3$ | $NHPr^n$ | N(OH)Me | H | 0 | |
| 1-73 | $CF_3$ | $NPr_2^n$ | N(OH)Me | H | 0 | |

TABLE 4-continued

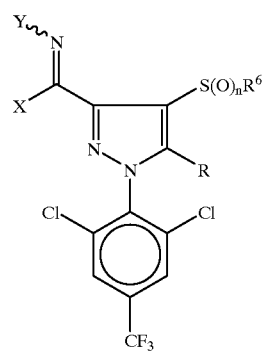

| Comp. No. | R⁶ | R | X | Y | n | mp. (° C.) |
|---|---|---|---|---|---|---|
| 1-74 | $CF_3$ | $NHPr^i$ | N(OH)Me | H | 0 | |
| 1-75 | $CF_3$ | $NHCH_2Ph$ | N(OH)Me | H | 0 | |
| 1-76 | $CF_3$ | $N(CH_2Ph)_2$ | N(OH)Me | H | 0 | |
| 1-77 | $CF_3$ | NHMe | N(OH)Me | H | 1 | |
| 1-78 | $CF_3$ | $NMe_2$ | N(OH)Me | H | 1 | 156–162 |
| 1-79 | $CF_3$ | NHEt | N(OH)Me | H | 1 | 220–227 |
| 1-80 | $CF_3$ | $NEt_2$ | N(OH)Me | H | 1 | 178–181 |
| 1-81 | $CF_3$ | $NHPr^n$ | N(OH)Me | H | 1 | |
| 1-82 | $CF_3$ | $NPr_2^n$ | N(OH)Me | H | 1 | |
| 1-83 | $CF_3$ | $NHPr^i$ | N(OH)Me | H | 1 | 154–156 |

TABLE 5

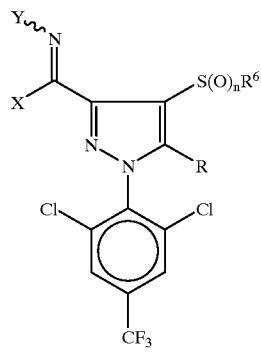

| Comp. No. | R⁶ | R | X | Y | n | mp. (° C.) |
|---|---|---|---|---|---|---|
| 1-84 | $CF_3$ | $NHCH_2Ph$ | N(OH)Me | H | 1 | |
| 1-85 | $CF_3$ | $N(CH_2Ph)_2$ | N(OH)Me | H | 1 | 81–84 |
| 1-86 | $CF_3$ | $NH_2$ | N(OH)Me | H | 2 | 181–183 |
| 1-87 | $CF_3$ | NHMe | N(OH)Me | H | 2 | |
| 1-88 | $CF_3$ | $NMe_2$ | N(OH)Me | H | 2 | |
| 1-89 | $CF_3$ | NHEt | N(OH)Me | H | 2 | 96–97 |
| 1-90 | $CF_3$ | $NEt_2$ | N(OH)Me | H | 2 | 166–167 |
| 1-91 | $CF_3$ | $NHPr^n$ | N(OH)Me | H | 2 | |
| 1-92 | $CF_3$ | $NPr_2^n$ | N(OH)Me | H | 2 | |
| 1-93 | $CF_3$ | $NHPr^i$ | N(OH)Me | H | 2 | |
| 1-94 | $CF_3$ | $NHCH_2Ph$ | N(OH)Me | H | 2 | |
| 1-95 | $CF_3$ | $N(CH_2Ph)_2$ | N(OH)Me | H | 2 | |
| 1-96 | $CF_3$ | $NH_2$ | $NH_2$ | $\underset{OCNHEt}{\overset{O}{\parallel}}$ | 1 | 211–215 |
| 1-97 | $CF_3$ | $NH_2$ | $NH_2$ | $\underset{OCCH_2Cl}{\overset{O}{\parallel}}$ | 1 | 196–197 |

TABLE 5-continued

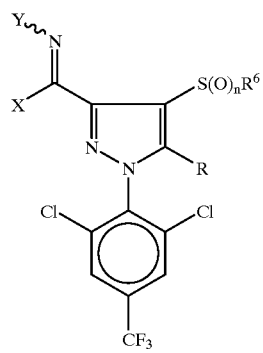

| Comp. No. | R⁶ | R | X | Y | n | mp. (° C.) |
|---|---|---|---|---|---|---|
| 1-98 | CF₃ | NH₂ | NH₂ | OCNMe₂ (O=) | 1 | (amorphous)[4] |
| 1-99 | CF₃ | NHCONHEt | NH₂ | OH | 1 | 196–198 |
| 1-100 | CF₃ | NHCOPh | NH₂ | OH | 2 | 152–154 |
| 1-101 | CF₃ | NHCOPh | NH₂ | OH | 1 | 219–221 |

[4]NMR (DMSO, δ) 2.98 (6H, s), 5.20 (2H, br), 5.43 (2H, br), 7.80 (2H, s)

TABLE 6

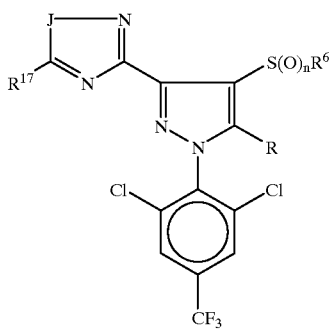

| Comp. No. | R⁶ | R | J | R¹⁷ | n | mp. (° C.) |
|---|---|---|---|---|---|---|
| 2-1 | Me | N=CH~OMe | O | H | 0 | 119–121 |
| 2-2 | CF₃ | NH₂ | O | H | 1 | 200–202 |
| 2-3 | CF₃ | NH₂ | O | Me | 1 | 221–223 |
| 2-4 | CF₃ | NH₂ | NH | H | 1 | 282–284 |
| 2-5 | CF₃ | NH₂ | NH | Me | 1 | |
| 2-6 | CF₃ | NH₂ | NMe | Me | 1 | |
| 2-7 | CF₃ | NH₂ | O | H | 2 | 205–208 |
| 2-8 | CF₃ | NH₂ | O | Me | 2 | |
| 2-9 | CF₃ | NH₂ | NH | H | 2 | |
| 2-10 | CF₃ | NH₂ | NH | Me | 2 | |
| 2-11 | CF₃ | NH₂ | NMe | Me | 2 | |
| 2-12 | CF₃ | NH₂ | O | H | 0 | 190–192 |
| 2-13 | CF₃ | N=CH~NHOH | O | H | 0 | 171–174 |
| 2-14 | CF₃ | N=CH~NHOH | O | H | 1 | 112–114 |
| 2-15 | CF₃ | N=CH~OMe | O | H | 1 | 137–139 |

TABLE 6-continued

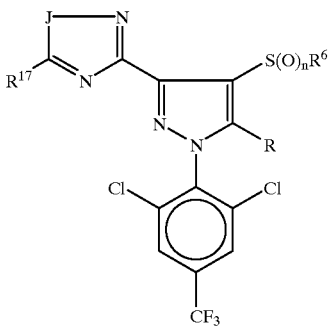

| Comp. No. | R⁶ | R | J | R¹⁷ | n | mp. (° C.) |
|---|---|---|---|---|---|---|
| 2-16 | CF₃ | N=CH~OMe | O | H | 2 | 157.5–158.5 |
| 2-17 | CF₃ | N=CH~OMe | O | H | 0 | 119–121 |
| 2-18 | CF₃ | N=CH~NHMe | O | H | 1 | 220–221 |
| 2-19 | CF₃ | N=CH~NMe₂ | O | H | 1 | 140–140.5 |
| 2-20 | CF₃ | NHCHO | O | H | 0 | 147–149 |
| 2-21 | CF₃ | NHCHO | O | H | 1 | 182–184 |

TABLE 7

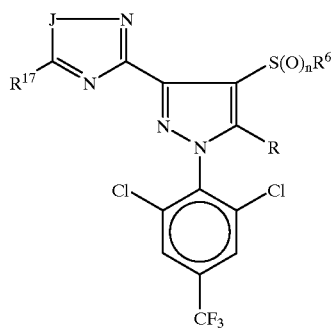

| Comp. No. | R⁶ | R | J | R¹⁷ | n | mp. (° C.) |
|---|---|---|---|---|---|---|
| 2-22 | $CF_3$ | NHMe | O | H | 0 | |
| 2-23 | $CF_3$ | $NMe_2$ | O | H | 0 | 95.5–97 |
| 2-24 | $CF_3$ | NHEt | O | H | 0 | 119–120 |
| 2-25 | $CF_3$ | $NEt_2$ | O | H | 0 | 94–95 |
| 2-26 | $CF_3$ | $NHPr^n$ | O | H | 0 | |
| 2-27 | $CF_3$ | $NPr_2^n$ | O | H | 0 | |
| 2-28 | $CF_3$ | $NHPr^i$ | O | H | 0 | |
| 2-29 | $CF_3$ | $NHCH_2Ph$ | O | H | 0 | |
| 2-30 | $CF_3$ | $N(CH_2Ph)_2$ | O | H | 0 | |
| 2-31 | $CF_3$ | NHMe | O | H | 1 | |
| 2-32 | $CF_3$ | $NMe_2$ | O | H | 1 | 82–84 |
| 2-33 | $CF_3$ | NHEt | O | H | 1 | 142.5–144 |
| 2-34 | $CF_3$ | $NEt_2$ | O | H | 1 | 117–119 |

TABLE 7-continued

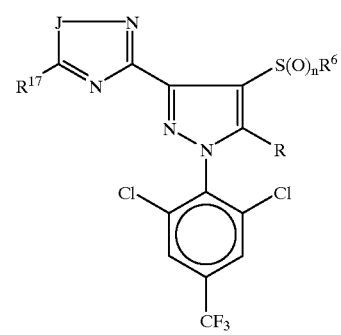

| Comp. No. | R⁶ | R | J | R¹⁷ | n | mp. (° C.) |
|---|---|---|---|---|---|---|
| 2-35 | $CF_3$ | $NHPr^n$ | O | H | 1 | |
| 2-36 | $CF_3$ | $NPr_2^n$ | O | H | 1 | |
| 2-37 | $CF_3$ | $NHPr^i$ | O | H | 1 | 133–134 |
| 2-38 | $CF_3$ | $NHCH_2Ph$ | O | H | 1 | |
| 2-39 | $CF_3$ | $N(CH_2Ph)_2$ | O | H | 1 | 126–127 |
| 2-40 | $CF_3$ | NHMe | O | H | 2 | 156.5–157.5 |
| 2-41 | $CF_3$ | $NMe_2$ | O | H | 2 | 140–142 |
| 2-42 | $CF_3$ | NHEt | O | H | 2 | 188–189 |
| 2-43 | $CF_3$ | $NEt_2$ | O | H | 2 | 177–179 |
| 2-44 | $CF_3$ | $NHPr^n$ | O | H | 2 | |
| 2-45 | $CF_3$ | $NPr_2^n$ | O | H | 2 | |

TABLE 8

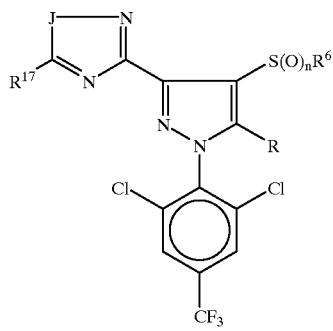

| Comp. No. | R⁶ | R | J | R¹⁷ | n | mp. (° C.) |
|---|---|---|---|---|---|---|
| 2-46 | $CF_3$ | $NHPr^i$ | O | H | 2 | |
| 2-47 | $CF_3$ | $NHCH_2Ph$ | O | H | 2 | |
| 2-48 | $CF_3$ | $N(CH_2Ph)_2$ | O | H | 2 | |
| 2-49 | $CF_3$ | NHAc | O | H | 2 | 163–164 |
| 2-50 | $CF_3$ | NHAc | O | H | 1 | 171–173 |
| 2-51 | $CF_3$ | $NHCO_2Me$ | O | H | 2 | 170–174 |
| 2-52 | $CF_3$ | N=CH~OEt | O | H | 1 | 88–90 |
| 2-53 | $CF_3$ | N=CH~OEt | O | H | 2 | 104–105 |
| 2-54 | $CF_3$ | $NHCO_2Me$ | O | H | 1 | 145–147 |
| 2-55 | $CF_3$ | N=C(Me)OMe | O | H | 1 | 108–109 |

TABLE 8-continued

| Comp. No. | R⁶ | R | J | R¹⁷ | n | mp. (° C.) |
|---|---|---|---|---|---|---|
| 2-56 | $CF_3$ | (3-OMe-4-OH-phenyl)-CH=N- | O | H | 0 | (amorphous)⁵⁾ |
| 2-57 | $CF_3$ | NHCONHEt | O | H | 1 | 166–168 |
| 2-58 | $CF_3$ | NHCOPh | O | H | 2 | 202–204 |
| 2-59 | $CF_3$ | EtO-CH=N- | O | H | 0 | 90–91.5 |
| 2-60 | $CF_3$ | NHAc | O | H | 0 | (amorphous)⁶⁾ |
| 2-61 | $CF_3$ | NHCOPh | O | H | 1 | 199–202 |
| 2-62 | $CF_3$ | (3-OMe-4-OH-phenyl)-CH=N- | O | H | 1 | (amorphous)⁷⁾ |

⁵⁾NMR (CDCl₃, δ) 3.89 (3H, s), 6.17 (1H, s), 6.98 (1H, d, J = 7.9 Hz), 7.30–7.37 (2H, m), 7.74 (2H, s), 8.88 (1H, s), 8.96 (1H, s)
⁶⁾NMR (CDCl₃, δ) 2.13 (3H, s), 7.30 (1H, br), 7.75 (2H, s), 8.88 (1H, s)
⁷⁾NMR (CDCl₃, δ) 3.82 (3H, s), 6.36 (1H, br), 6.94 (1H, d, J = 8.2 Hz), 7.22 (1H, d, J = 1.8 Hz), 7.34 (1H, dd, J = 1.8 Hz, 8.2 Hz), 7.73–7.75 (1H, m), 7.78–7.80 (1H, m)

TABLE 9

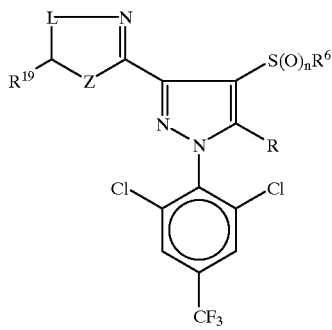

| Comp. No. | R⁶ | R¹⁹ | R | Z | L | n | mp. (° C.) |
|---|---|---|---|---|---|---|---|
| 3-1 | CF₃ | H | NH₂ | NH | CH₂ | 1 | (amorphous)[8] |
| 3-2 | CF₃ | H | NH₂ | NH | CH₂CH₂ | 1 | |
| 3-3 | CF₃ | H | NH₂ | NH | CH₂ | 2 | |
| 3-4 | CF₃ | H | NH₂ | NH | CH₂CH₂ | 2 | |
| 3-5 | CF₃ | H | NH₂ | NH | O | 1 | 126–130 |
| 3-6 | CF₃ | Me | NH₂ | NH | O | 1 | (amorphous)[9] |
| 3-7 | CF₃ | Et | NH₂ | NH | O | 1 | (amorphous)[10] |
| 3-8 | CF₃ | H | NH₂ | NH | O | 0 | 178–179 |
| 3-9 | CF₃ | H | NHMe | NH | O | 0 | |
| 3-10 | CF₃ | H | NMe₂ | NH | O | 0 | |
| 3-11 | CF₃ | H | NHEt | NH | O | 0 | |
| 3-12 | CF₃ | H | NEt₂ | NH | O | 0 | |
| 3-13 | CF₃ | H | NHPrⁿ | NH | O | 0 | |
| 3-14 | CF₃ | H | NPr₂ⁿ | NH | O | 0 | |
| 3-15 | CF₃ | H | NHPrⁱ | NH | O | 0 | |
| 3-16 | CF₃ | H | NHCH₂Ph | NH | O | 0 | |
| 3-17 | CF₃ | H | N(CH₂Ph)₂ | NH | O | 0 | |

[8] NMR (DMSO, δ) 3.75 (4H, br), 5.22 (3H, br), 7.80 (2H, s)
[9] NMR (DMSO, δ) 1.52 and 1.54 (3H, d + d, J = 5.1 Hz), 5.00 (1H, br), 5.18 diastereomer (2H, br), 5.83 (quint, J = 5.1 Hz, 1H), 7.81 (s, 2H) mixture
[10] NMR (DMSO, δ) 0.95–1.05 (3H, m), 1.72–1.83 (2H, m), 5.0 (1H, br), diastereomer 5.22 (2H, br), 5.64 (1H, q, J = 5.0 Hz), 7.81 (2H, s) mixture

TABLE 10

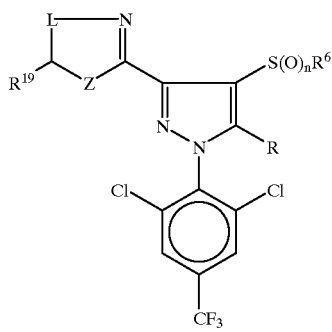

| Comp. No. | R⁶ | R¹⁹ | R | Z | L | n | mp. (° C.) |
|---|---|---|---|---|---|---|---|
| 3-18 | $CF_3$ | H | NHMe | NH | O | 1 | |
| 3-19 | $CF_3$ | H | $NMe_2$ | NH | O | 1 | |
| 3-20 | $CF_3$ | H | NHEt | NH | O | 1 | |
| 3-21 | $CF_3$ | H | $NEt_2$ | NH | O | 1 | |
| 3-22 | $CF_3$ | H | $NHPr^n$ | NH | O | 1 | |
| 3-23 | $CF_3$ | H | $NPr_2^n$ | NH | O | 1 | |
| 3-24 | $CF_3$ | H | $NHPr^i$ | NH | O | 1 | |
| 3-25 | $CF_3$ | H | $NHCH_2Ph$ | NH | O | 1 | |
| 3-26 | $CF_3$ | H | $N(CH_2Ph)_2$ | NH | O | 1 | |
| 3-27 | $CF_3$ | H | $NH_2$ | NH | O | 2 | 202–204 |
| 3-28 | $CF_3$ | H | NHMe | NH | O | 2 | |
| 3-29 | $CF_3$ | H | $NMe_2$ | NH | O | 2 | |
| 3-30 | $CF_3$ | H | NHEt | NH | O | 2 | |
| 3-31 | $CF_3$ | H | $NEt_2$ | NH | O | 2 | |
| 3-32 | $CF_3$ | H | $NHPr^n$ | NH | O | 2 | |
| 3-33 | $CF_3$ | H | $NPr_2^n$ | NH | O | 2 | |
| 3-34 | $CF_3$ | H | $NHPr^i$ | NH | O | 2 | |
| 3-35 | $CF_3$ | H | $NHCH_2Ph$ | NH | O | 2 | |
| 3-36 | $CF_3$ | H | $N(CH_2Ph)_2$ | NH | O | 2 | |
| 3-37 | $CF_3$ | H | N=CH~OMe | NH | O | 1 | 201–204 |

TABLE 11

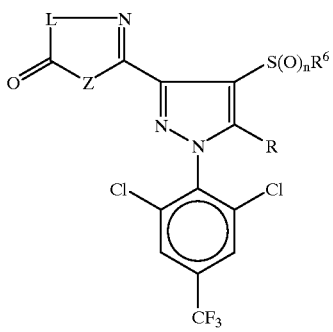

| Comp. No. | R⁶ | R | Z | L | n | mp. (° C.) |
|---|---|---|---|---|---|---|
| 4-1 | $CF_3$ | $NH_2$ | NH | O | 1 | 270–273 (dec.)[11] |

[11] NMR (DMSO, δ) 7.06 (2H, br), 8.22 (2H, s), 13.22 (1H, br)

TABLE 12

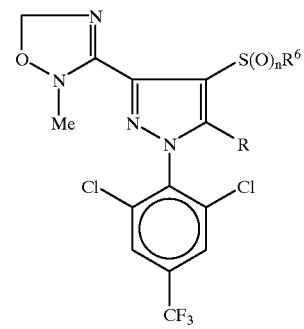

| Comp. No. | R⁶ | R | n | mp. (° C.) |
|---|---|---|---|---|
| 5-1 | $CF_3$ | $NH_2$ | 0 | |
| 5-2 | $CF_3$ | NHMe | 0 | |
| 5-3 | $CF_3$ | $NMe_2$ | 0 | |
| 5-4 | $CF_3$ | NHEt | 0 | |
| 5-5 | $CF_3$ | $NEt_2$ | 0 | |
| 5-6 | $CF_3$ | $NHPr^n$ | 0 | |
| 5-7 | $CF_3$ | $NPr_2^n$ | 0 | |
| 5-8 | $CF_3$ | $NHPr^i$ | 0 | |

TABLE 13

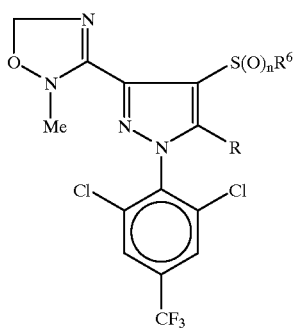

| Comp. No. | R⁶ | R | n | mp. (° C.) |
|---|---|---|---|---|
| 5-9 | $CF_3$ | $NHCH_2Ph$ | 0 | |
| 5-10 | $CF_3$ | $N(CH_2Ph)_2$ | 0 | |
| 5-11 | $CF_3$ | $NH_2$ | 1 | 165–167 |
| 5-12 | $CF_3$ | NHMe | 1 | |
| 5-13 | $CF_3$ | $NMe_2$ | 1 | |
| 5-14 | $CF_3$ | NHEt | 1 | |
| 5-15 | $CF_3$ | $NEt_2$ | 1 | |
| 5-16 | $CF_3$ | $NHPr^n$ | 1 | |
| 5-17 | $CF_3$ | $NPr_2{}^n$ | 1 | |
| 5-18 | $CF_3$ | $NHPr^i$ | 1 | |
| 5-19 | $CF_3$ | $NHCH_2Ph$ | 1 | |
| 5-20 | $CF_3$ | $N(CH_2Ph)_2$ | 1 | |
| 5-21 | $CF_3$ | $NH_2$ | 2 | |
| 5-22 | $CF_3$ | NHMe | 2 | |
| 5-23 | $CF_3$ | $NMe_2$ | 2 | |
| 5-24 | $CF_3$ | NHEt | 2 | |
| 5-25 | $CF_3$ | $NEt_2$ | 2 | |
| 5-26 | $CF_3$ | $NHPr^n$ | 2 | |
| 5-27 | $CF_3$ | $NPr_2{}^n$ | 2 | |
| 5-28 | $CF_3$ | $NHPr^i$ | 2 | |
| 5-29 | $CF_3$ | $NHCH_2Ph$ | 2 | |
| 5-30 | $CF_3$ | $N(CH_2Ph)_2$ | 2 | |

EXAMPLE 23

An emulsifiable concentrate was produced by sufficiently mixing the compound No. 1-1 (20% by weight), xylene (75% by weight) and polyoxyethylene glycol ether (Nonipol 85 (trade name)) (5% by weight).

EXAMPLE 24

A wettable powder was produced by sufficiently mixing the compound No. 1-1 (30% by weight), sodium lignin sulfonate (5% by weight), polyoxyethylene glycol ether (Nonipol 85 (trade name)) (5% by weight), white carbon (30% by weight) and clay (30% by weight).

EXAMPLE 25

A dust was produced by sufficiently mixing the compound No. 1-1 (3% by weight), white carbon (3% by weight) and clay (94% by weight).

EXAMPLE 26

A granule was produced by mixing the compound No. 1-1 (10% by weight), sodium lignin sulfonate (5% by weight) and clay (85% by weight) with pulverizing, adding water and kneading them, followed by granulating and further drying.

EXAMPLE 27

An insecticidal dust was produced by sufficiently mixing the compound No. 1-1 (1.275% by weight), cartap (2.2% by weight), white carbon (0.5% by weight) and clay (96.025% by weight).

EXAMPLE 28

An insecticidal/fungicidal dust was produced by sufficiently mixing the compound No. 1-1 (1.275% by weight), validamycin (0.33% by weight), white carbon (0.5% by weight) and clay (97.895% by weight).

Test Example 1
Insecticidal Effect Against *Chilo Suppressalis*

Five milligrams each of test compounds (designated by each compound number assigned to the compound prepared in the above-described Examples) were respectively dissolved in 0.5 ml of acetone containing Tween 20 (trade name) and diluted with a 3,000-fold aqueous solution of Dyne to a predetermined concentration (100 ppm). This solution was applied to the leaves and stems of young rice seedlings at the 2 to 3-leaf stage raised in a nursery box (planting of 6 to 7 stubs) at a rate of 20 ml/pot by a spray gun. After the solution was dried, the young rice seedlings were put into a test tube (φ: 3 cm, h: 20 cm) together with 5 ml of tap water. After the relase of ten 3-instar larvae of *Chio suppressalis* to the test tube. The test tube was placed in an incubator (27° C.). After five days, the total of the dead larvae was counted and the damage was observed. The mortality was calculated by the following equation:

Mortality (%)=(number of the dead larvae/number of the applited larvae)×100.

The damage of young rice seadlings was evaluated according to the following criteria:

| Damage | Criteria |
|---|---|
| 0 | The damage is scarcely recognized. |
| 1 | The damage is slightly recognized (not more than about 1/10 of non-treated young seedlings). |
| 2 | The damage is recognized less than about ½ of non-treated young seedlings. |
| 3 | The damage is recognized not less than about ½ of non-treated young seedlings. |
| 4 | The damage equivalent to non-treated young seedlings is recognized. |

The result is shown in Table 14.

TABLE 14

| Comp. No. | Mortality (%) | Damage to young rice seedlings |
|---|---|---|
| 1-1 | 100 | 0 |
| 1-2 | 100 | 0 |
| 1-3 | 100 | 0 |
| 1-4 | 100 | 0 |
| 1-11 | 100 | 0 |
| 1-12 | 100 | 0 |
| 1-29 | 100 | 0 |
| 1-30 | 100 | 0 |
| 1-35 | 100 | 0 |
| 1-36 | 100 | 0 |
| 1-37 | 100 | 0 |
| 1-39 | 100 | 0 |
| 1-49 | 100 | 0 |
| 1-58 | 100 | 0 |
| 1-59 | 100 | 0 |
| 1-67 | 100 | 0 |
| 1-69 | 100 | 0 |
| 1-86 | 100 | 0 |
| 2-1 | 100 | 0 |
| 2-2 | 100 | 0 |

TABLE 14-continued

| Comp. No. | Mortality (%) | Damage to young rice seedlings |
|---|---|---|
| 2-3 | 100 | 0 |
| 2-4 | 100 | 0 |
| 2-7 | 100 | 0 |
| 2-12 | 100 | 0 |
| 2-14 | 100 | 0 |
| 2-15 | 100 | 0 |
| 2-16 | 100 | 0 |
| 2-19 | 100 | 0 |
| 2-21 | 100 | 0 |
| 2-23 | 100 | 0 |
| 2-32 | 100 | 0 |
| 2-40 | 100 | 0 |
| 2-41 | 100 | 0 |
| 2-49 | 100 | 0 |
| 2-52 | 100 | 0 |
| 2-53 | 100 | 0 |
| 2-59 | 100 | 0 |
| 3-1 | 100 | 0 |
| 3-5 | 100 | 0 |
| 3-6 | 100 | 0 |
| 3-8 | 100 | 0 |
| 3-27 | 100 | 0 |
| 3-38 | 100 | 0 |
| 4-1 | 100 | 0 |
| 5-11 | 100 | 0 |

From Table 14, it was shown that the compound [I] of the present invention have excellent insecticidal activities and are excellent compounds having no damage.

Industrial Applicability

1-Arylpyrazole derivatives [I] or their salts of the present invention have excellent insecticidal activities and less toxicity against fishes. Therefore, the insecticidal compositions containing the compound [I] or a salt thereof of the present invention protect crops, etc. from harmful pests and can contribute to an agricultural success.

What is claimed is:

1. A compound of the formula (I)

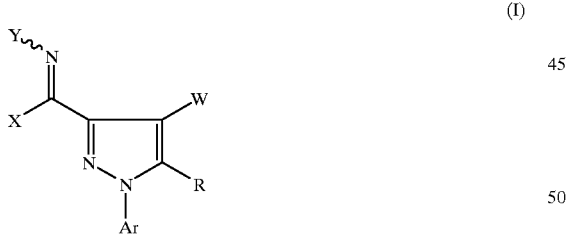

wherein

Ar is a $C_{6-14}$ aromatic hydrocarbon group which may optionally be substituted, wherein when the $C_4$ position is substituted, the substituent is a trifluoromethyl group;

R is a group selected from
(a) nitro,
(b) a group of the formula: —$NR^1R^2$ wherein $R^1$ and $R^2$ each are independently
  (1) hydrogen,
  (2) a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group, which may optionally be substituted with 1 to 5 substituents selected from group (A) consisting of 1) nitro, 2) hydroxyl, 3) oxo, 4) thioxo, 5) cyano, 6) carbamoyl, 7) carboxyl, 8) $C_{1-15}$ acyl, 9) sulfo, 10) halogen, 11) $C_{1-14}$ alkoxy which may optionally be mono- to tri-substituted with halogen, 12) —$S(O)_{n''}R^a$ wherein n" is 0, 1 or 2, $R^a$ is a $C_{1-6}$ alkyl or $C_{6-14}$ aryl, 13) amino which may optionally be mono- or di-substituted with $C_{1-6}$ alkyl or $C_{1-6}$ alkyl-carbonyl, 14) imino which may optionally be substituted with $C_{1-6}$ alkyl, hydroxy or $C_{1-6}$ alkoxy, 15) hydrazono which may optionally be mono- or di-substituted with $C_{1-4}$ alkyl and 16) 5- or 6-membered heterocyclic group having 1 to 4 hetero atoms selected from O, S and N in addition to carbon atom(s), which may optionally be substituted with 1 to 4 substituents selected from halogen, $C_{1-4}$ alkyl and mono- to tri-halogenated phenoxy, (3) a $C_{1-15}$ acyl group which may optionally be substituted with 1 to 5 substituents selected from the group (A), (4) a carbamoyl group which may optionally be substituted with a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group, which may optionally be substituted with 1 to 5 substituents selected from the group (A), (5) 3- to 8-membered heterocyclic group having 1 to 4 hetero atoms selected from N, O and S in addition to carbon atom(s), which may be condensed with a $C_{5-10}$ cyclic hydrocarbon ring or 5- or 6-membered heterocyclic ring and may optionally be substituted with 1 to 6 substituents selected from group (B) consisting of 1) a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-14}$ aryl group and $C_{7-15}$ aralkyl group, which may optionally be mono- to tri-substituted with halogen, 2) $C_{1-14}$ alkoxy, 3) $C_{1-15}$ acyl, 4) $C_{1-15}$ acyloxy, 5) carbamoyl which may optionally be mono- or di-substituted with $C_{1-4}$ alkyl, 6) cyclic aminocarbonyl, 7) halogen, 8) oxo, 9) amidino, 10) imino which may optionally be substituted with $C_{1-6}$ alkyl, 11) amino which may optionally be mono- or di-substituted with $C_{1-6}$ alkyl, carbamoyl or N-mono- or N, N-di-$C_{1-4}$ alkyl-carbamoyl, 12) 3- to 6-membered cyclic amino having carbon atom(s) and one nitrogen and optionally, 1 to 3 hetero atoms selected from O,S and N, 13) $C_{1-6}$ alkanoylamido, 14) benzamido, 15) $C_{1-3}$ alkylenedioxy, 16) —$B(OH)_2$, 17) hydrozyl, 18) nitro, 19)syano, 20) —$S(O)_{n''}r^b$ wherein n" is 0, 1 or 2 and $R^b$ is hydrogen, a $C_{1-6}$ alkyl or $C_{6-14}$ aryl, 21) sulfamoyl which may optionally be mono- or di-substituted with $C_{1-6}$ alkyl, and 22) carboxyl, (6) hydroxyl, (7) a $C_{1-20}$ alkoxy which may optionally be substituted with 1 to 5 substituents selected from the group (A) or (8) —$SO_pR^8$ wherein $R^8$ is hydrogen, or a hydrocarbon group selected from the group of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group, which may optionally be substituted with 1 to 5 substituents selected from the group (A), p is 1 or 2, (c) 3- to 8-membered heterocyclic group having a chemical bond at a nitrogen atom and 1 to 4 hetero atoms selected from N, O and S in addition to carbon atom(s) and one nitrogen atom, which may be condensed with a $C_{5-10}$ cyclic hydrocarbon ring or 5- or 6-membered heterocyclic ring and may optionally be substituted with 1 to 6 substituents selected from the group (B), and (d) a group of the formula: —N=C($R^3$)$R^4$ wherein $R^3$ and $R^4$ each are independently 1) hydrogen, 2) a hydrocarbon group selected from the group of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group, which may optionally be substituted with 1 to 5 substituents selected from the group (A), 3) a $C_{1-20}$ alkoxy which may optionally be substituted with 1 to 5 substituents selected from the group (A) or 4) —NR$^9$R$^{10}$ wherein $R^9$ and $R^{10}$ each are hydrogen, hydroxyl or a hydrocarbon group selected from the group of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group, which may optionally be substituted with 1 to 5 substituents selected from the group (A);

W is a group represented by a group of the formula: —S(O)$_n$R$^6$ wherein $R^6$ is (1) a hydrocarbon group selected from the group of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group, which may optionally be substituted with 1 to 5 substituents selected from the group (A) or (2) 3- to 8-membered heterocyclic group having 1 to 4 hetero atoms selected from N, O and S in addition to carbon atom(s), which may be condensed with a $C_{5-10}$ cyclic hydrocarbon ring or 5- or 6-membered heterocyclic ring and may be substituted with 1 to 6 substituents selected from the group (B), n is an integer of 0 to 2;

X is amino,

Y is hydroxyl, or

X and Y are combined, such that the compound of the formula (I) is:

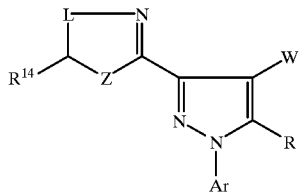

wherein $R^{14}$ is hydrogen or a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group, which may optionally be substituted; L is oxygen; and Z is —NR$^{15}$— wherein $R^{15}$ is hydrogen or a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-16}$ aryl group, and $C_{7-15}$ aralkyl group, which may optionally be substituted with 1 to 5 substituents selected from the group (A), or a salt thereof.

2. The compound according to claim 1, wherein X and Y are combined, such that the compound of formula (I) is:

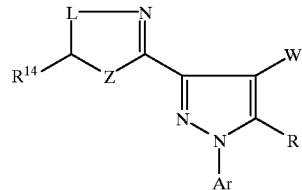

wherein $R^{14}$ is hydrogen; L is oxygen; and Z is —NR$^{15}$— wherein $R^{15}$ is hydrogen or a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-16}$ aryl group, and $C_{7-15}$ aralkyl group, which may optionally be substituted with 1 to 5 substituents selected from the group (A).

3. The compound according to claim 1, wherein Ar is 2,6-dichloro-4-trifluoromethylphenyl.

4. The compound according to claim 1, wherein R is (i) a group of the formula: —NR$^{1b}$R$^{2b}$ wherein $R^{1b}$ and $R^{2b}$ each are (a) hydrogen, (b) a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group which may optionally be substituted with 1 to 3 substituents selected from the group (A), (c) a $C_{1-7}$ acyl group which may optionally be substituted with 1 to 3 substituents selected from the group (A) or (d) a mono- or di-$C_{1-4}$ alkyl-carbamoyl group which may optionally be substituted with 1 to 3 substituents selected from the group (A), or (ii) a group of the formula: —N=C($R^{3b}$)$R^{4b}$ wherein $R^{3b}$ and $R^{4b}$ each are (a) hydrogen, (b) $C_{1-15}$ alkyl, (c) $C_{6-14}$ aryl which may optionally be substituted with $C_{1-4}$ alkoxy and/or hydroxyl, (d) $C_{1-15}$ alkoxy, or (e) mono- or di-$C_{1-15}$ alkylamino or hydroxyamino.

5. The compound according to claim 4, wherein $R^{1b}$ and $R^{2b}$ each are hydrogen, $C_{1-6}$ alkyl, $C_{7-15}$ aralkyl, mono- or di-$C_{1-4}$ alkyl-carbamoyl or $C_{1-7}$ acyl, $R^{3b}$ is hydrogen or $C_{1-6}$ alkyl, and $R^{4b}$ is $C_{1-4}$ alkoxy, $C_{6-14}$ aryl, mono- or di-$C_{1-4}$ alkylamino or hydroxyamino.

6. The compound according to claim 1, wherein W is a group of the formula: —S(O)$_n$R$^6$ wherein $R^6$ is a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group, which may optionally be substituted with 1 to 5 substituents selected from the group (A), or an optionally substituted heterocyclic group, and n is an integer of 0 to 2.

7. The compound according to claim 6, wherein $R^6$ is a $C_{1-6}$ alkyl group which may optionally be mono- to tetra-substituted with halogen.

8. The compound according to claim 1, wherein X and Y are combined, such that the compound of formula (I) is:

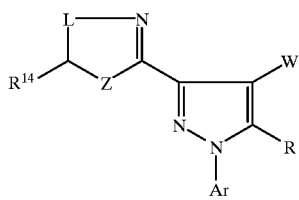

wherein $R^{14}$ is hydrogen or a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-14}$ aryl group, and $C_{7-15}$ aralkyl group which may optionally be substituted; L is oxygen; and Z is —$NR^{15}$— wherein $R^{15}$ is hydrogen or a hydrocarbon group selected from the group consisting of $C_{1-6}$ alkyl group, $C_{2-6}$ alkenyl group, $C_{2-6}$ alkynyl group, $C_{3-6}$ cycloalkyl group, $C_{6-16}$ aryl group, and $C_{7-15}$ aralkyl group, which may optionally be substituted with 1 to 5 substituents selected from the group (A).

9. The compound according to claim 1, wherein $R^{14}$ and $R^{15}$ each are hydrogen or a $C_{1-6}$ alkyl group which may optionally be substituted.

10. The compound according to claim 1, which is 5-amino-1-(2,6-dichloro-4-trifluoromethylphenyl)-4-trifluoromethylsulfinyl-3-pyrazolecarboxamide oxime, 5-amino-1-(2,6-dichloro-4-trifluoromethylphenyl)-3-(4H-1,2,4-oxadiazolin-3-yl)-4-trifluoromethylsulfinylpyrazole, or a salt thereof.

11. An agrochemical composition which comprises an effective amount of the compound as defined in claim 1 or a salt thereof together with a liquid or solid carrier.

12. An insecticidal composition comprising an effective amount of the compound as defined in claim 1 or a salt thereof together with a liquid or solid carrier.

13. A method of controlling an insect, which comprises applying an effective amount of the compound as defined in claim 1, or a salt thereof, to an area in which an insect may be located.

14. A process for producing the compound as defined in claim 1 or a salt thereof which comprises:

reacting a compound of the formula:

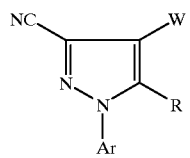

wherein Ar, R and W are as defined in claim 1, or a salt thereof with a compound of the formula:

Q—$NH_2$ wherein Q is hydroxyl, to produce a compound of the formula:

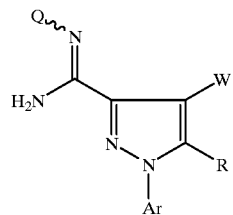

wherein Ar, R and W are as defined in claim 1, and Q is as defined above, or a salt thereof.

* * * * *